United States Patent
Schecter

(10) Patent No.: US 7,963,925 B1
(45) Date of Patent: Jun. 21, 2011

(54) METHOD AND APPARATUS FOR DEFINING THE EFFECT OF ATRIAL ARRHYTHMIAS ON CARDIAC PERFORMANCE AND DIRECTING THERAPY USING A PLURALITY OF INTRINSICALLY AND EXTRINSICALLY DERIVED SIGNALS

(76) Inventor: Stuart O. Schecter, Great Neck, NY (US)

( * ) Notice: Subject to any disclaimer, the term of this patent is extended or adjusted under 35 U.S.C. 154(b) by 905 days.

(21) Appl. No.: 11/686,602

(22) Filed: Mar. 15, 2007

Related U.S. Application Data

(63) Continuation of application No. 11/584,465, filed on Oct. 20, 2006, now abandoned, which is a continuation-in-part of application No. 11/334,935, filed on Jan. 19, 2006, now abandoned.

(60) Provisional application No. 60/647,102, filed on Jan. 26, 2005, provisional application No. 60/660,101, filed on Mar. 9, 2005.

(51) Int. Cl.
*A61B 5/02* (2006.01)

(52) U.S. Cl. ........................... 600/508; 600/527

(58) Field of Classification Search ............... 600/508, 600/527
See application file for complete search history.

(56) References Cited

U.S. PATENT DOCUMENTS

| | | | |
|---|---|---|---|
| 3,184,842 A | 5/1965 | Maropis | |
| 4,019,073 A | 4/1977 | Vishnevsky et al. | |
| 4,210,837 A | 7/1980 | Vasiliev et al. | |
| 4,844,062 A | 7/1989 | Wells | |
| 5,389,865 A | 2/1995 | Jacobus et al. | |
| 5,429,604 A | 7/1995 | Hammersmark et al. | |
| 5,484,433 A | 1/1996 | Taylor et al. | |
| 5,549,650 A | 8/1996 | Bornzin et al. | |
| 5,628,777 A | 5/1997 | Moberg et al. | |
| 5,693,074 A | 12/1997 | Ferec-Petric | |
| 5,769,640 A | 6/1998 | Jacobus et al. | |
| 5,771,902 A | 6/1998 | Lee et al. | |
| 5,833,623 A | 11/1998 | Mann et al. | |
| 5,836,946 A | 11/1998 | Diaz et al. | |
| 5,971,931 A | 10/1999 | Raff | |
| 6,059,759 A | 5/2000 | Mottola et al. | |
| 6,070,100 A | 5/2000 | Bakels et al. | |
| 6,077,236 A | 6/2000 | Cunningham | |

(Continued)

OTHER PUBLICATIONS

Office Action issued in a corresponding U.S. Appl. No. 11/848,346, Dec. 22, 2010.

(Continued)

*Primary Examiner* — Scott M Getzow
*Assistant Examiner* — Joseph M Dietrich
(74) *Attorney, Agent, or Firm* — Gottlieb, Rackman & Reisman, P.C.

(57) ABSTRACT

This invention describes methods and algorithms for processing a plurality of relevant signals/data intrinsic to a patient and/or derived from external diagnostic equipment for management of atrial arrhythmias. The intrinsic signals are acquired from intracardiac leads/sensors and analogous extrinsic data obtained from imaging equipment and patient demographics. These data are input into software algorithms that use digital signal processing to output informational data of clinical and technical relevance after comparisons are made to patients with access to this technology whose outcome under varying treatments is known. These combined data are used to define prognosis, make treatment suggestions, direct programming of cardiac devices and digitally convert intrinsically and extrinsically derived indices into a common metric. In a preferred embodiment, the intrinsically and extrinsically acquired data is utilized in the design of catheters and software algorithms for performing intracardiac procedures such as ablation of atrial arrhythmias.

8 Claims, 25 Drawing Sheets

U.S. PATENT DOCUMENTS

| | | | |
|---|---|---|---|
| 6,304,777 | B1 | 10/2001 | Ben-Haim et al. |
| 6,418,346 | B1 | 7/2002 | Nelson et al. |
| 6,572,560 | B1 | 6/2003 | Watrous et al. |
| 6,574,511 | B2 | 6/2003 | Lee |
| 6,628,988 | B2 | 9/2003 | Kramer et al. |
| 6,641,480 | B2 | 11/2003 | Murzanski et al. |
| 6,725,091 | B2 | 4/2004 | Dal Molin |
| 6,740,033 | B1 | 5/2004 | Olejniczak et al. |
| 6,780,183 | B2 | 8/2004 | Jimenez, Jr. et al. |
| 6,792,308 | B2 | 9/2004 | Corbucci |
| 6,795,732 | B2 | 9/2004 | Stadler et al. |
| 6,804,559 | B1 | 10/2004 | Kraus et al. |
| 6,805,667 | B2 | 10/2004 | Christopherson et al. |
| 6,816,301 | B1 | 11/2004 | Schiller |
| 6,826,509 | B2 | 11/2004 | Crisco, III et al. |
| 6,906,700 | B1 | 6/2005 | Armstrong |
| 7,063,671 | B2 * | 6/2006 | Couvillon, Jr. ............... 600/562 |
| 7,139,621 | B2 | 11/2006 | Gharsalli |
| 2002/0026103 | A1 | 2/2002 | Norris et al. |
| 2002/0072784 | A1 | 6/2002 | Sheppard, Jr. et al. |
| 2002/0120188 | A1 * | 8/2002 | Brock et al. ................. 600/407 |
| 2003/0083702 | A1 | 5/2003 | Stadler et al. |
| 2003/0216620 | A1 | 11/2003 | Jain et al. |
| 2004/0019285 | A1 | 1/2004 | Eigler et al. |
| 2004/0111127 | A1 | 6/2004 | Gliner |
| 2004/0153128 | A1 | 8/2004 | Suresh et al. |
| 2004/0167587 | A1 | 8/2004 | Thompson |
| 2004/0176679 | A1 | 9/2004 | Murphy et al. |
| 2005/0043895 | A1 | 2/2005 | Schechter |
| 2005/0059876 | A1 | 3/2005 | Krishnan et al. |
| 2005/0182447 | A1 | 8/2005 | Schecter |
| 2005/0241026 | A1 | 10/2005 | Esler et al. |
| 2005/0280508 | A1 | 12/2005 | Mravca et al. |
| 2007/0103437 | A1 | 5/2007 | Rosenberg |
| 2007/0197939 | A1 | 8/2007 | Wallace et al. |
| 2007/0233044 | A1 | 10/2007 | Wallace et al. |
| 2008/0009759 | A1 | 1/2008 | Chetham |
| 2008/0119871 | A1 | 5/2008 | Brock et al. |
| 2009/0312814 | A1 | 12/2009 | Schecter |

OTHER PUBLICATIONS

Makoto Shimojo et al., A High-Speed Mesh of Tactile Sensors Fitting Arbitrary Serface, IEEE Sensor Journal, vol. 10, No. 4, Apr. 2010.

Allison M. Okamura et al., Reality-Based Models for Vibration Feedback in Virtual Environments, IEEE/ASME Transactions on Mechatronics, vol. 6, No. 3, Sep. 2001.

Office Action issued in related U.S. Appl. No. 11/746,752, Mailed Apr. 5, 2010.

Farrokh Janabi-Sharifi et al., Discrete-Time Adaptive Windowing for Velocity Estimation, IEEE/ASME Transactions on Control Systems Technology, vol. 8, No. 6, Nov. 2000.

Young Qin er al., Microfibre-nanowire Hybrid Structure for Energy Scavenging, School of Materials Science and Engineering, Georgia Institute of Technology, Atlanta, Georgia, USA, vol. 451, Feb. 2008.

S. Stramigioli et al., A Novel Theory for Sample Data System Passivity, IEEE/RSJ, International Conference of Intelligent Robots and Systems, EPFL, Lausanne, Switzerland, Oct. 2002.

Honjie Leng et al., Development of a Novel Deformation-Based Tissue Softness Sensor, IEEE Sensors Journal, vol. 9, No. 5, May 2009.

J. E. Colgate et al., Factors Affecting the Z-Width of a Haptic Display, IEEE, Department of Mechanical Engineering, Northwestern University, 2145 Sheridan Rd., Evanston, Illinois , 1994.

J. E. Colgate et al., Passivity of a Class of Sampled-Data Systems: Application to Haptic Interfaces, IEEE, Department of Mechanical Engineering, Northwestern University, 2145 Sheridan Rd., Evanston, Illinois , Journal of Robotic Systems, John Wiley & Sons, Inc., 1997.

Dipen C. Shah et al., Area Under the Real-Time Contact Force Curve (Force-Time Integral) Predicts Radiofrequency Lesion Size in an Vitro Contractile Model, Journal of Cardiovascular Electrophysiology, vol. No. 10, pp. 1-5.

Dissertation of Katherine Julianne Kuchenbecker, 2006.

* cited by examiner

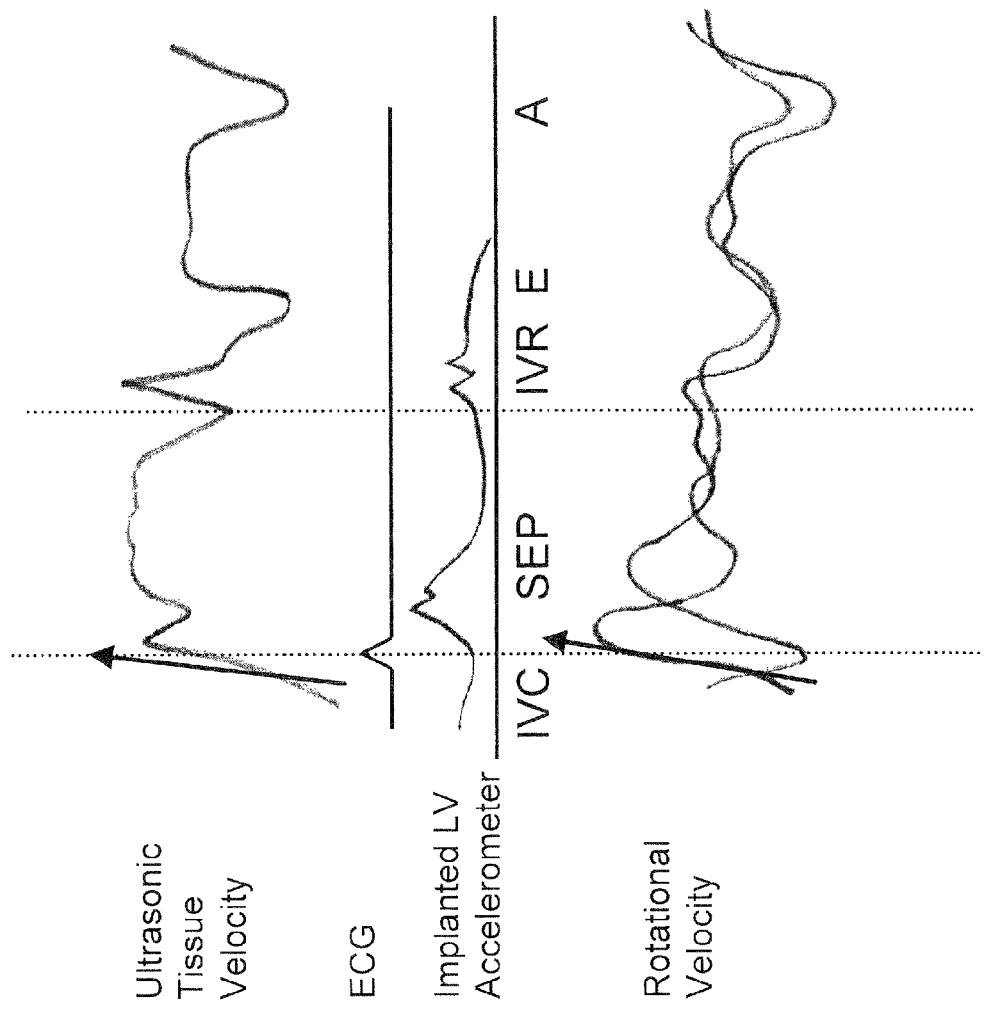

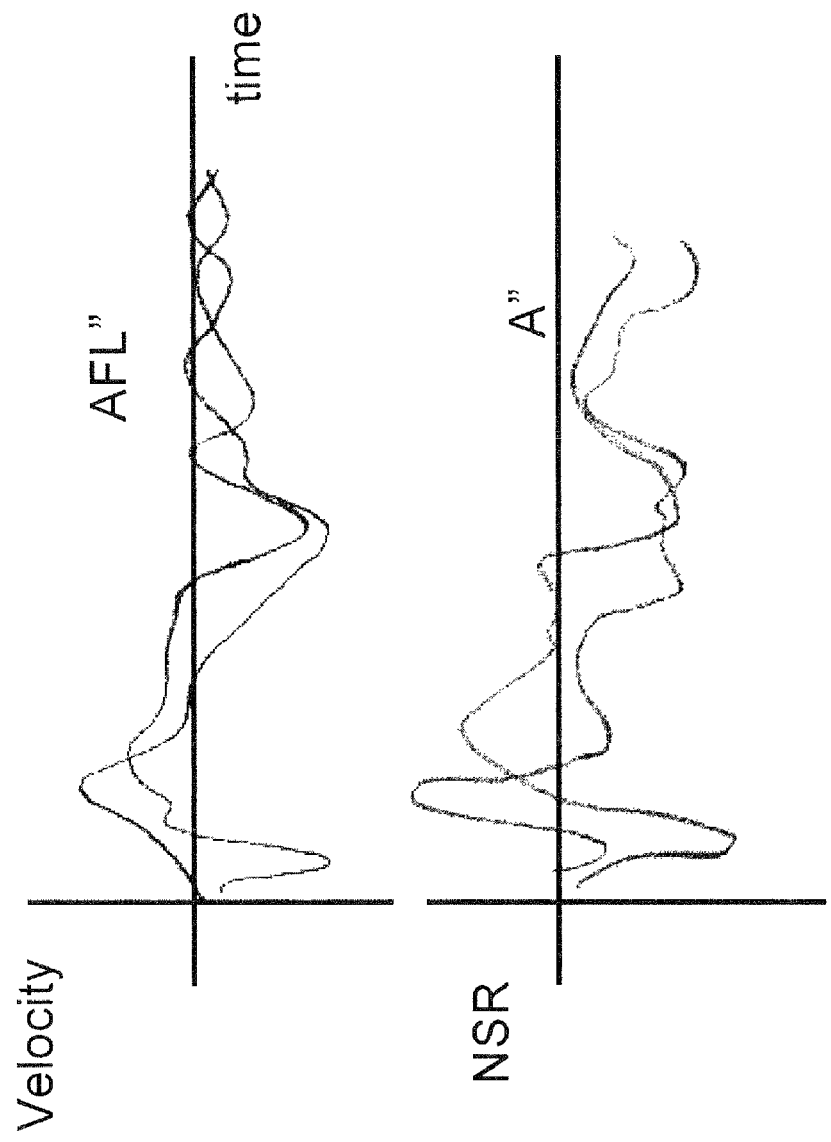

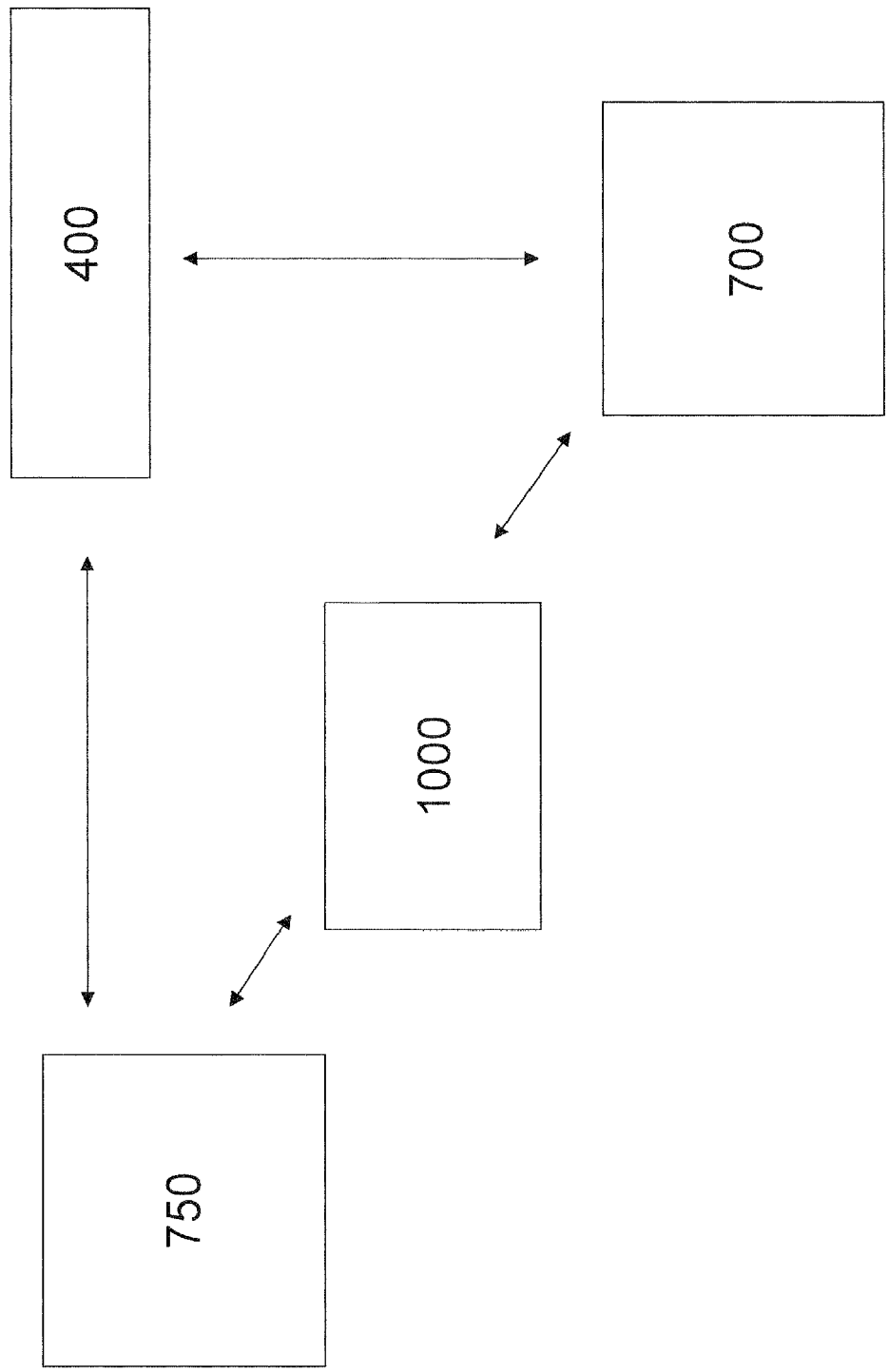

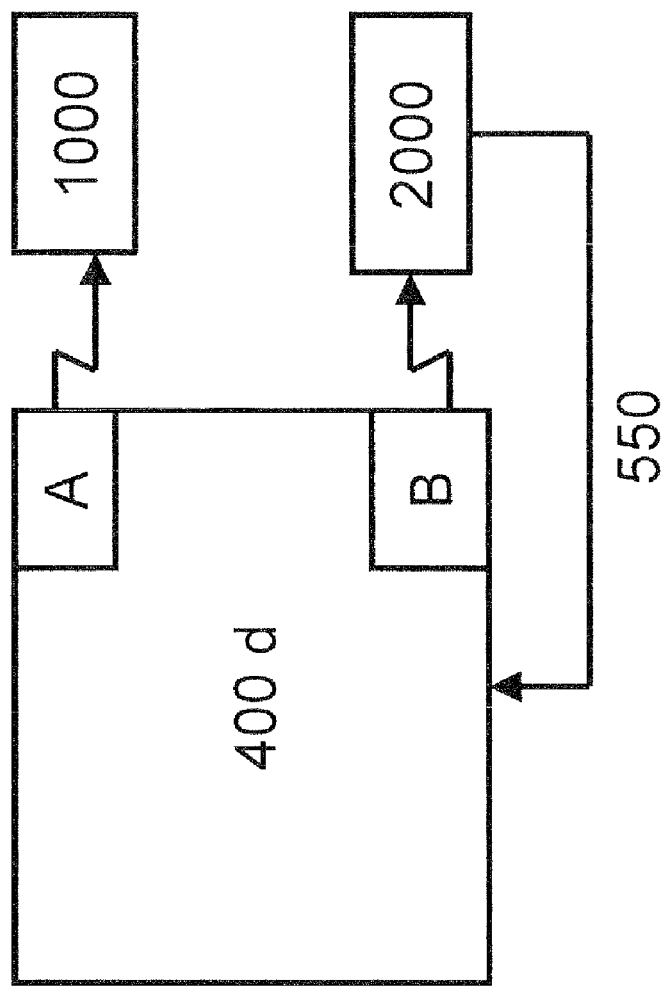

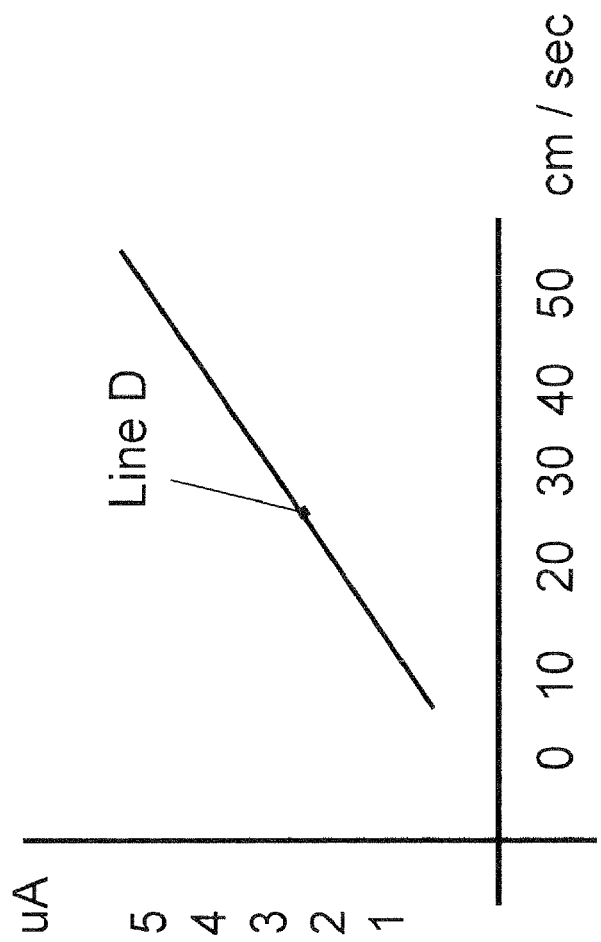

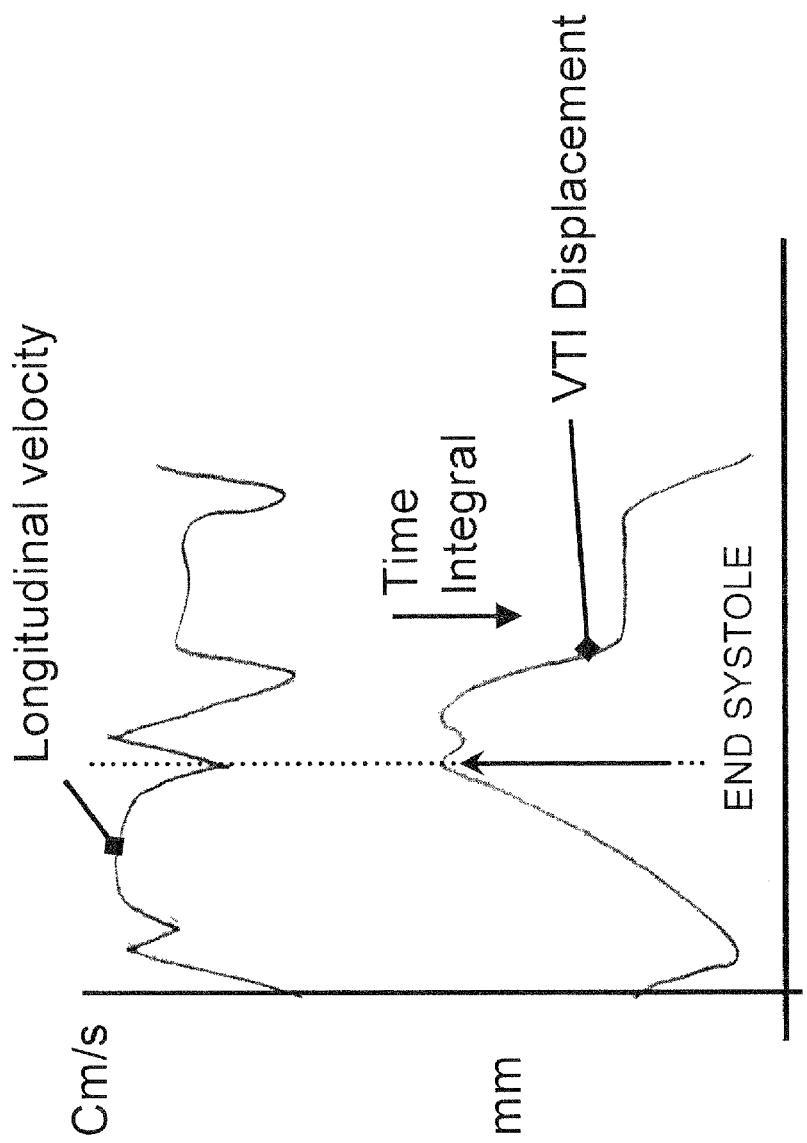

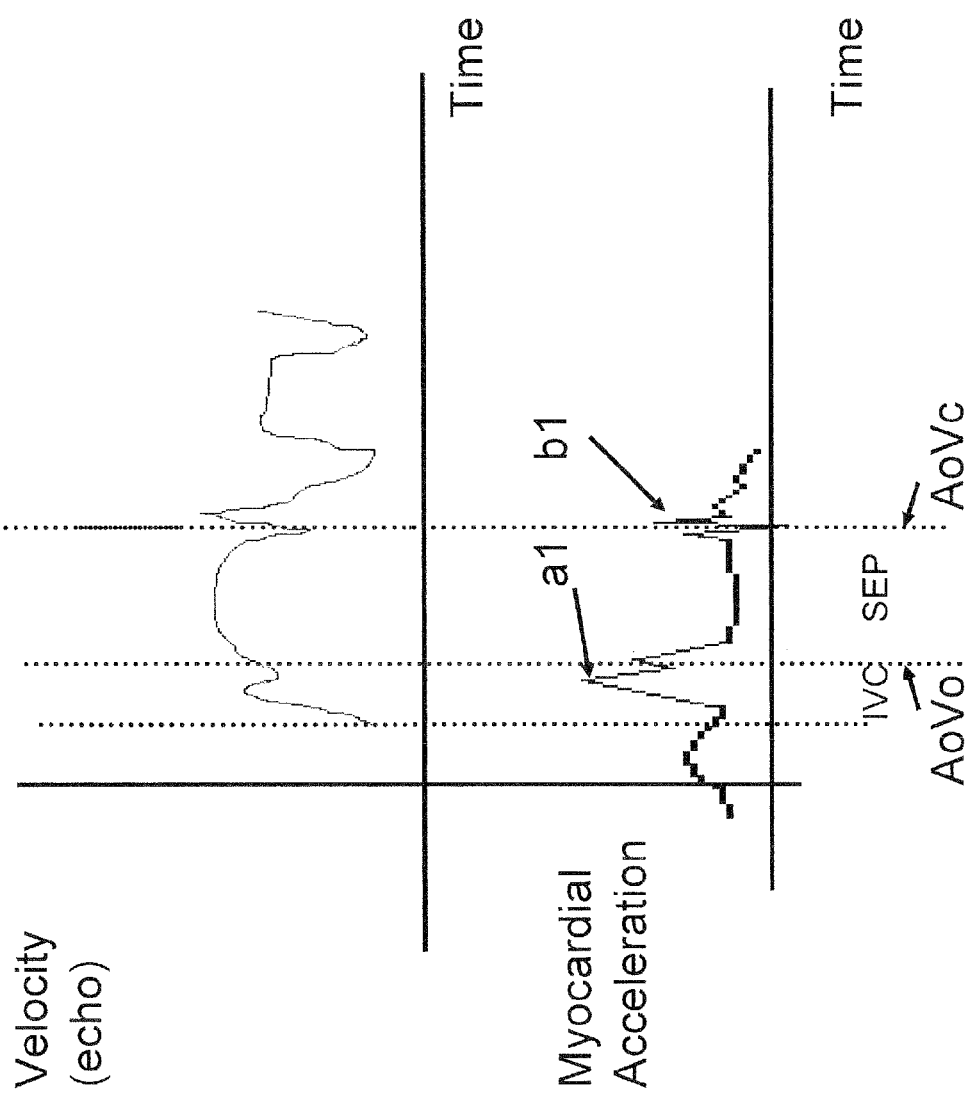

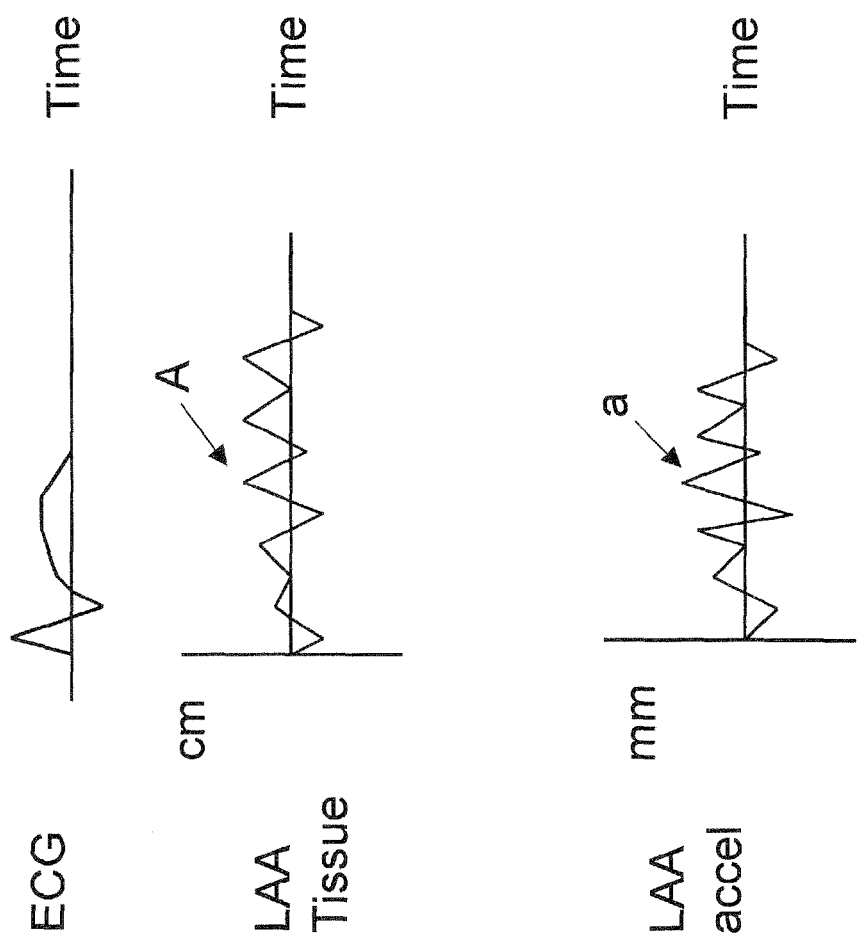

LA – left atrium
LAA – left atrial appendage
MV – mitral valve
LV – left ventricle
PV – left upper pulmonary vein
C – common wall
f – free wall

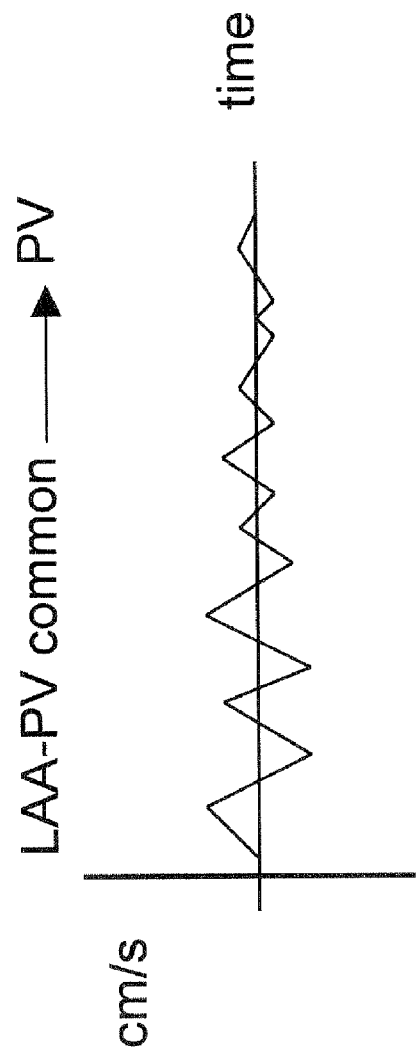

METHOD AND APPARATUS FOR DEFINING THE EFFECT OF ATRIAL ARRHYTHMIAS ON CARDIAC PERFORMANCE AND DIRECTING THERAPY USING A PLURALITY OF INTRINSICALLY AND EXTRINSICALLY DERIVED SIGNALS

This patent application claims priority to provisional patent applications Nos. 60/647,102 filed Jan. 26, 2005; and 60/660,101 filed Mar. 9, 2005. This patent application is also a Continuation of U.S. application Ser. No. 11/584,465, filed Oct. 20, 2006, now abandoned, which is a continuation-in-part of U.S. application Ser. No. 11/334,935, filed Jan. 19, 2006, now abandoned. Priority is claimed to all of these applications, and all are incorporated herein by reference.

BACKGROUND OF THE INVENTION

Field of the Invention

Description of the Prior Art

Normal atrial function is important for effective cardiac performance. In patients with compromised cardiac function (e.g. cardiomyopathy), the presence of atrial arrhythmias is associated with a poor prognosis. Normal sinus rhythm is known to contribute to cardiac output and the absence of normal sinus rhythm can reduce cardiac stroke volume by more than 10 percent. This can render a patient with impaired cardiac performance unstable (e.g. congestive heart failure, hypotension). Likewise, in patients without significant impairments in cardiac performance atrial arrhythmias cause symptoms that affect quality of life, and lead to adverse outcomes including cerebrovascular accidents. Effective treatment of atrial arrhythmia will improve cardiac performance, reduce morbidity/mortality, decrease hospitalizations and improve quality of life. Accurate identification of the pathologic state of the heart affected by atrial arrhythmias by analysis of a plurality of physiologic factors will better direct treatment and result in improved patient outcome.

This application pertains to a system and apparatus for evaluating atrial arrhythmia and determining the status and prognosis of a patient and more particularly to a system and apparatus wherein measurements from the patient are combined with external information such as statistical information collected from other patients and results of diagnostic testing to obtain a diagnosis, treatment options and prognostic information for the patient quickly and accurately using evidence based medicine. Such derived information is applied to make recommendations for both acute and chronic management of atrial arrhythmias in any particular patient. The acute data guides procedural treatment of atrial arrhythmias whereas the chronic data is used for making recommendations about long-term therapies.

Major advances are occurring in the development of imaging modalities, invasive cardiac procedures and implantable technologies capable of diagnosing and treating a variety of pathophysiologic states. Thus, the clinician has numerous diagnostic tests at his or her disposal and an option of therapeutic regimens. Coupled with the wealth of information from these tests, there is a need to expeditiously evaluate the results of a plethora of diagnostic tests, and compare the data to historical data sets. Treatment algorithms designed to assess such informational data sets will better direct therapy (evidence-based medicine).

To a large extent, practice decisions based on anecdotal data and individual studies have dictated medical practice to date. However, large scale population studies and the development of registries along with digitization of acquired diagnostic data obtained from these studies provide more powerful statistical analyses of patient outcome by comparing differing therapeutic modalities. The availability of such data will depend on a means for device-device communication and the evolution of wide range digitization of medical records and of data derived from different diagnostic equipment. Though the majority of the algorithms and examples described herein are in reference to advances in cardiovascular medicine, the inventions described have broad range application to any medical field and are particularly applied to treatment of atrial arrhythmias.

The advent of digital signal processing (DSP) in evolving technologies (e.g. implantable pacemaker/defibrillators) allow for informational data sets to be available in discrete numeric format, processed by high-speed microprocessors, and incorporated into software algorithms. Such processing allow a user to relate, in a complementary fashion, clinically relevant data obtained from both an imaging apparatus and implanted device as to derive a composite of information for diagnostic purposes and for optimizing patient management. The application of DSP enables calculation algorithms to perform several processing operations simultaneously.

The following references provide background information for the present application and illustrate the state of the art. All these references are incorporated by reference.

U.S. Pat. Nos.:
6,804,559, 6,795,732, 6,792,308, 6,816,301, 6,572,560, 6,070,100, 6,725,091, 6,628,988, 6,740,033, 5,971,931, 5,833,623, 6,826,509, 6,805,667, 6,574,511, 6,418,346, 5,549,650, 6,077,236, 5,628,777, 5,693,074, 6,906,700

Published US patent applications:
20040176810, 20030083702, 20020026103, 20040111127, 20020072784, 20030216620, 20040167587, 20050182447, 20050043895, 20040186465

References in peer-reviewed journals:
Hocini M, Sanders P, Jais P et al. Techniques for Curative Treatment of Atrial Fibrillation. Journal of Cardiovascular Electrophysiology, Vol. 15, No. 12, December 2004, p 1467.
Oral H, Pappone C, Chugh A. Circumferential Pulmonary Vein Ablation for Chronic Atrial Fibrillation. NEJM 354:9, Mar. 2, 2006, p 934.
Nademmanee K, Mckenzie J, Koar E, et al. A New Approach for Catheter Ablation of Atrial Fibrillation: Mapping of the Electrophysiologic Substrate. JACC Vol 43, No. 11, 2004. p 2044.
Gonzalez M D, Otomo K, Shah N. Transeptal Left Heart Catheterization for Cardiac Ablation Procedures. J Interventional Cardiac electrophysiology 2001. 5, 89-95.
Pappone C, Santinelli V. The Who, What, Why and How-to Guide for Circumferential Pulmonary Vein Ablation. J Cardiovascular Electrophysiolgy 2004. Vol 15, 1226-1230.
Meluzin Jaroslav, Novak Miroslav, Mullerova Jolana, Krejci Jan, Hude Petr, Eisenberger Martin, Dusek Ladislav, Dvorak, Ivo, Spinarova Lenka, A fast and simple echocardiographic method of determination of the optimal atrio-ventricular delay in patients after biventricular stimulation. PACE, 2004. 27: p. 58-64.
Padeletti L, Barold S S. Digital Technology for Cardiac Pacing. Am J Cardiolo 2005; 95: 479-482.
Thomas J D, Greenberg N L, Garcia M J. Digital echocardiography 2002: now is the time. J Am Soc Echocardiography 2002; 15: 831-8.

Feignebaum H. Digital echocardiography [review]. Am J Cardiology 2000; 86: 2G-3G.

SUMMARY OF THE INVENTION

In the parent application identified above, software algorithms for readily evaluating a number of variables descriptive of cardiac performance and electromechanical dysynchrony (physiological properties) are provided assimilated within an implanted device or downloaded between implanted, intrinsic sensors/transducers and a separate apparatus/extrinsic diagnostic equipment (e.g. echocardiography machine, cardiac MRI). In this application the same algorithms are applied for evaluating variables descriptive of atrial arrhythmias within an implanted device/catheter based system and extrinsic diagnostic equipment such as echocardiography machines as to guide treatment of atrial arrhythmias. A composite of physiological properties obtained from intrinsic sensors/transducers is digitized (if necessary) and compared to normal and pathologic values as to generate physiological descriptors that have a numerical score. Models constructed to predict probability of outcome from the data obtained can be implemented for such comparisons (Selker et al. Patient specific predictions of outcomes in myocardial infarction for real-time emergency use: a thrombolytic predictive instrument. Ann Intern med 1997; 127: 538-56). These physiologic descriptors are then input into software algorithms as to produce an informational data set of clinical and technical relevance that guides physician management. This informational data set (IDS) is output in form of an easily interpretable set of recommendations or prognostic data for the clinician. In one embodiment, such IDS can be downloaded into removable digital storage media or other media compatible with implanted device software and incorporated into an electronic medical record (EMR). Neural networks are applied to these algorithms to teach the system at periodic intervals. In a preferred embodiment, the IDS is available to closed loop control systems that direct therapies (e.g. atrial overdrive pacing, catheter based ablation) aimed at treating a specific pathologic state (e.g. atrial fibrillation).

Specific therapies are identified for treating atrial arrhythmias. Such therapies include but are not limited to long-term anticoagulation, anti-arrhythmic drugs, and/or catheter ablation of atrial arrhythmias. Implanted sensors/transducers from CRM devices provide data about a given patients pathologic state and in conjunction with extrinsically derived data assist decision-making about which treatment will have the optimal risk:benefit ratio. Similarly, implanted sensors/transducers from temporarily implanted catheter based sensors/transducers during ablation therapy of atrial arrhythmia can be combined with extrinsic data as well. Closed loop control systems that incorporate both intrinsically and extrinsically derived data are implemented rendering an ablation procedure more effective, safer and less timely.

The present invention relates to acquiring a plurality of diagnostic information based on intrinsic properties of a given patient and extrinsic information derived from diagnostic testing performed on the patient, and combining the available data to derive prognostic information about atrial arrhythmias using evidence based medicine. Recommendations for therapy delivered intrinsically via an implanted device/catheter based system or extrinsically via various therapeutic modalities are made with such analysis algorithms. The algorithms generate informational data sets for diagnostic/monitoring purposes with the object of guiding physician management and/or programming of a permanently implanted device or ablation apparatus via a closed loop control system. Such informational data sets may be also used, for example, to guide titration of pharmaceutical therapies, identify risk factors for stroke and thromboembolism or a patient's candidacy for ablation therapy, cardiac rhythm management (CRM) device implantation or even open heart procedures (e.g. mitral valve replacement, MAZE procedure). This technology is also capable of incorporating downloadable indices/data from extrinsic diagnostic equipment into implanted devices/programmers and vice versa at periodic intervals via removable digital media (e.g. removable hard drive, magnetic-optical disc) or wireless telemetry (e.g. Bluetooth). Bi-directional communication of this data is used to confirm adequate functioning of an implanted device and verify diagnoses made with extrinsic equipment (cross-verification). This data can be examined to predict response to specific therapeutic modalities such as anti-arrhythmic therapy, anti-coagulation, CRM device implantation or ablation procedures.

Diagnostic imaging modalities use digitization with standardization of storage format adherent to standard models (Digital Imaging and Communication in Medicine). Thus, there is a need to formulate composite indices which can be digitally processed and input into fast software algorithms for processing. Extrinsically derived composite indices can be evaluated from time to time and compared to similar indices generated from implanted sensors/transducers (intrinsic), assimilated into an implanted device or other apparatus's existing diagnostic data. Translation of units of expression (i.e. as mathematical indices) derived from signals acquired by intracardiac sensors/transducers into conventional indices commonly used with external imaging modalities will facilitate device-device communication and interpretability.

Through the utilization of this invention, a means of translation between analogous intrinsic/extrinsic indices is developed from the acquired pooled data after significant numbers of patients gain access to these technologies, though this can be performed for each individual patient as well. The concepts underlying this invention are extended to electrocardiographic monitoring, imaging technologies including, but not limited to, echocardiography, magnetic resonance imaging, PET scans, nuclear imaging or computed tomography, and other diagnostic/laboratory tests. The extrinsically derived composite data is downloadable into an implanted device for storage (e.g. medical record keeping) and available to the clinician in combination with similarly derived device based indices. The combined informational data set (intrinsic and extrinsic) can then more accurately provide prognostic information and generate recommendations for various therapies (e.g. using neural networks). Comparisons between extrinsic and intrinsic diagnostic data is used to confirm diagnoses (e.g. electromechanical dysynchrony as the etiologic cause of mitral regurgitation leading to atrial fibrillation).

A method and means for correlating intrinsically and extrinsically derived data with a translation function is developed once large numbers of patients have access to these technologies and patient outcome under varying clinical circumstances is determined. Digitization and standardization of storage formats will facilitate the application of such a translation function for derivation of analogous intrinsic and extrinsic indices using a universal mathematical language that will provide the clinician with prognostic information and treatment suggestions. Through open connectivity and the translation function, neural networks are applied to teach the system how to recreate a representation of intracardiac anatomy based on analyses of a plurality of acquired data.

Ultrasonic Techniques

Current ultrasound technologies allow for a means of evaluating changes in regional volume, differential myocardial motion and contractility. Temporal frame rates for evaluating such subtle differences in timing are currently under 10 milliseconds. Available equipment manufactured by a number of companies such as General Electric, Philips, TomTec and Siemens are capable of measuring changes in both global and regional volumes within the cardiac chambers during the cardiac cycle. Analysis of tissue Doppler data allows for calculation of tissue velocities, myocardial strain and strain rate derived from the spatial gradient of tissue velocity (strain rate equation). This can also be performed by defining relative locations of ultrasound reflectors in two or three dimensional space over time using a technique referred to as speckle tracking (GE). Such data is currently processed at fast enough rates as to generate real time parametric imaging. With current day processing and microprocessor robustness, a number of analyses (unique and redundant) can be performed simultaneously in digital format and be able to be compiled into informational data sets used for diagnostic purposes.

Physiologic Properties/Data Input

The present invention provides for a rapid interpretation of physiological properties such as intracardiac geometry (G), valvular function (V) electromechanical dysynchrony (DI) and properties of tissue motion (M) as to generate relevant information, IDS, to the physician who is considering delivering a specific therapy for atrial arrhythmias (e.g. treatment with anti-arrhythmic therapy, anticoagulation, ablation therapy). Any available index or index to be defined may be incorporated into algorithms for performing such tasks and those mentioned in this application are by way of example. Data including but not limited to demographic information, hematologic profiles and genotype can also be input into these algorithms.

Application to Digital Devices—Interfacing/Telemetry

Currently implanted pacemakers/defibrillators which rely on analog technology are evolving into devices that universally transform all analog signals into digital format. This will allow data compression and storage of extensive amounts of information in digital libraries within the device. Transfer of relevant clinical data (informational data set) between imaging equipment and implanted devices through digital technology is then easily accomplished. This transfer may be by direct connection or wireless telemetry sent to implanted devices and device programmers. Security measures to ensure compliance with HIPAA regulations may require the use of fixed network addresses that place restrictions on access to such data. The clinical utility of the methods and algorithms described herein will be best realized when digital processing operations occurring within implanted devices and extrinsic diagnostic equipment occur expeditiously and in a standardized format.

BRIEF DESCRIPTION OF THE DRAWINGS

FIG. 2 depicts velocity (myocardial acceleration—arrows) as a function of time as detected by an implanted lead based accelerometer (middle) and with tissue Doppler imaging (longitudinal—top; rotational—bottom).

FIG. 3 illustrates how atrial tachyarrhythmias can affect LV rotation via global tethering affects FIG. 4 demonstrates wireless bi-directional communication between a central processing center, CPC, at 1000 and implanted devices at 750/external diagnostic equipment at 700 and peripheral, internal processing center, 400. Periodic updates of monitored indices/data and patient therapies/outcome are sent to the central processing center from individual patients and such pooled data is then transmitted and incorporated back into an internal processing center, contained within the implanted device and/or extrinsic diagnostic equipment or as stand alone equipment.

FIG. 6 demonstrates how data in a device based processing center, 400d, has wireless communication with a central processing center, CPC, at 1000 and health care provider, HCP, 2000. Such communication can be open or selectively controlled by switches (A and B) activated by the following physician.

FIG. 7 shows a linear relationship, line D, between an intrinsically derived parameter of cardiac tissue displacement based on accelerometer derived device based data and one derived extrinsically using tissue Doppler imaging. The mathematical relationships of analogous intrinsic and extrinsic data is used to derive equations that serve to mathematically translate analogous intrinsically derived and extrinsically derived indices that are representative of prognosis and patient response to differing therapies. Regression analysis or other statistical techniques are utilized to define such relationships along a graduated numerical scale.

FIG. 8 illustrates longitudinal velocity time graph, top; integration of velocity time graph for derivation of displacement, bottom;

FIG. 9 depicts the temporal relationship between tissue Doppler derived velocity time graph on top and implanted lead based accelerometer derived myocardial acceleration time graph on the bottom. One cardiac cycle is illustrated, wherein AoVo=aortic valve opening, AoVc=aortic valve closure.

FIG. 17 e illustrates how this dampening apparatus, Damp, functions along the central axis of the catheter (double headed arrow).

FIG. 17 f illustrates an intracardiac tactile exploration system composed of whiskers W1-W4, centrally located—deployable ablation apparatus, RFA, and strain gauges, SG.

FIG. 17 g depicts an alternate intracardiac tactile exploration system design.

DETAILED DESCRIPTION OF THE INVENTION

The methods described herein serve to optimize cardiac performance in patients with atrial arrhythmias. Intrinsic properties such as hematologic profiles, patient/family history, cardiac tissue velocity/displacement and intracardiac blood flow are combined with extrinsic properties such as anatomic and functional descriptors of the heart (e.g. cardiac chamber sizes/geometry, pulmonary vein anatomy) and measurements of systolic and diastolic cardiac performance (e.g. left ventricular function).

Figure 1:
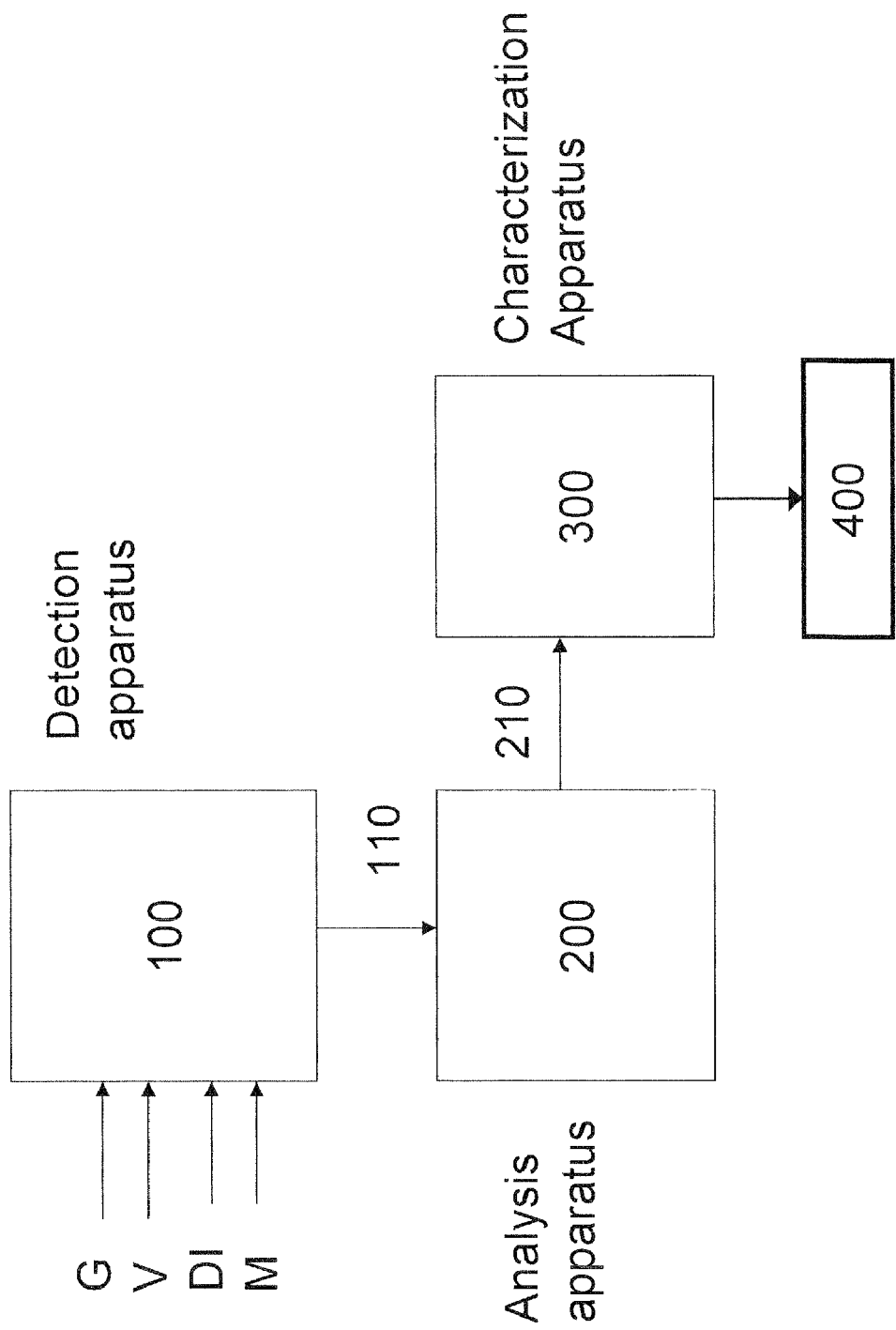
FIG. 1 shows a block diagram for handling information in accordance with this invention.

Referring to FIG. 1, intrinsic and extrinsic physiological properties, G, V, DI and M are collected and digitized by the Detection Apparatus, 100. Apparatus 100 may be an external unit, part of a device programmer or contained within an implanted device itself. Any number of properties may be input to 100. By way of example, G may be atrial size, V mean atrial appendage velocity, DI relates to atrial-ventricular and intra-ventricular dysynchrony and M severity of mitral regurgitation (MR) based on echocardiography or even cardiac acoustics (e.g. stethoscope) or externally located (extrinsic) or implanted (intrinsic) acoustical transducer. V can be derived intrinsically via lead based accelerometer derived indices of atrial tissue motion or echocardiographic determination of left atrial appendage mean velocity. Specific demographic information including prognostically relevant hematologic characteristics (e.g. concentration of specific clotting factors) may be entered into 100 as well. Internally derived properties may be analyzed and compared to analogous extrinsically derived physiological properties that are input into 100, as described in more detail below.

In one embodiment of the invention, these characteristics are defined using monitoring technologies within implanted cardiac devices, such as frequency and duration of atrial fibrillation (AF burden) or sensor determination of systolic and diastolic cardiac performance. These characteristics are compiled from numerous patients and evaluated as pooled data to correlate clinical outcome/prognosis based on various physiologic properties, relevant demographics and patient diagnostic information. Within implanted devices, algorithms for preventing atrial arrhythmias such as overdrive pacing are modified based on such data and documented responses to various over-drive pacing schemes in various patient subgroups.

In the parent application, these characteristics determined how to program interval timing in a CRT device. These characteristics were also used to determine the duration and frequency of activation of novel pacing modalities such as CCM or alternate NPIT. In this application these characteristics are also derived from external monitoring equipment, (e.g. M, G), and are incorporated into reference/template data in digital format for comparison to real time acquired data (e.g. frequency and duration of atrial arrhythmias, imparted motion of cardiac tissue from atrial arrhythmias to intracardiac catheters/leads), in the Analysis Apparatus, 200. These physiological properties are assigned a numerical value along a graduated scale and output from 200 as physiological descriptors, 210. These intrinsically and/or extrinsically derived physiologic characteristics will ultimately determine how an implanted device or other cardiac therapeutic device functions in a closed loop system (e.g. atrial fibrillation suppression algorithms). Recommendations are made to a physician on how to manage patient medication regimens and guide therapy both chronically and acutely, as will be described below.

Atrial fibrillation (AF) is the most common arrhythmia effecting millions of patients. Treatment directed toward reducing symptoms and the sequelae of AF will vary depending on a given individuars risk profile. For example, anticoagulation with medications that reduce clotting and risk for stroke also increase risk for bleeding complications that can be life threatening. The medications commonly prescribed can inhibit platelets from clotting (e.g. aspirin) or inhibit certain circulating coagulation factors in the bloodstream (e.g. Warfarin). Data from large population trials (Stroke Prevention in Atrial Fibrillation or SPAF) using evidence based medicine has shown that patients with certain risk factors (e.g. increased age, history of hypertension, left ventricular hypertrophy, cardiomyopathy) have a significantly lower risk of having a stroke from atrial fibrillation if treated with Warfarin than with an anti-platelet agent. In patients within these subgroups treatment with Warfarin outweighs risk. Within these subgroups of patients, however, other subgroups of patients can be found to have various risk profiles and more specific predictive analyses may be made. For, example, the presence or absence of certain hematologic clotting factors, the actual size and geometry of the atrial chambers and motion characteristics of atrial tissue further defines risk profile. Genetic factors and family history of thromboembolism are other intrinsic factors that relate to risk of stroke. Extrinsically derived factors include echocardiographic measurements of the atrial and ventricular chambers, velocity of blood flow and velocity of cardiac tissue/myocardium within the cardiac chambers (e.g. right and/or left atrial appendage) and indices of systolic/diastolic cardiac performance. These extrinsically derived factors are commonly measured with echocardiography and are entered into the algorithms described herein, stored in a central processing center along with data from other subgroups of patients and ultimately provide more specific guidelines for treatment of atrial fibrillation.

Intrinsically derived, device based indices include atrial fibrillation burden, episode duration and frequency. Patient risk for stroke depends on these indices, but guidance is needed as to determine the best therapy for specific patient subgroups (e.g. Warfarin, aspirin, AF ablation). Long-term studies are needed to better risk stratify patients in different sub-groups. Use of evidence based medicine by combining extrinsically and intrinsically derived data for outcome analysis of a large population of patients will improve disease management.

Atrial fibrillation burden is a measurement of the amount of time a given patient is having AF. The greater the amount of time and longer the duration of the episodes of AF, the greater the risk for stroke or other thromboembolic phenomena. When such data is combined with echocardiographic measurements, hematologic measurements, genotype and the like, more precise recommendations are made for any given individual patient. In this way, the most appropriate treatment options can be pursued (e.g. specific pacing modalities aimed at preventing recurrent AF are programmed into a CRM device).

As mentioned above, blood flow and cardiac tissue velocity is measurable with echocardiography. Conventional echocardiography is used to assess the velocity of blood flow from the atrial chambers into the ventricular chambers (measurement of diastolic function). More specifically, the mitral A wave relates to the velocity of blood flow during atrial contraction and the mitral E wave relates to passive diastolic filling. Pathologic increases and decreases in the amplitude of this blood flow (diastolic abnormality) can confer greater risk of thromboembolism. For example, significant increases in the amplitude of the A wave is seen in patients with stiff, non-compliant hearts that are hypertrophic and decreases in the amplitude of the A wave can be seen in patients who lack atrial transport. Both conditions suggest an increased risk of stroke from intermittent or paroxysmal atrial arrhythmias. Similar E and A waves can be acquired by myocardial tissue Doppler techniques (e.g. mitral annular velocity) or even implanted accelerometers for quantification of a variety of physiologic properties. These concepts are well known in cardiology practice.

A more specific means of determining risk would entail measuring the actual blood flow (velocity) within the left atrial appendage (LAA). The LAA is known to be the source of thromboembolism in AF in the far majority of embolic strokes. Reductions in LAA blood flow velocity (<20 cm/sec) as measured by transesophageal echocardiography (TEE) are associated with increased risk of stroke.

Characteristics of mitral inflow (A wave) and LAA flow are entered into databases and used for guiding treatment options for patients with atrial arrhythmia. Acquired data from permanently or temporarily implanted leads or catheters can provide analogous information (e.g. lead based accelerometer detection of myocardial motion characteristic of arrhythmia and intracardiac or transesophageal echocardiographic pulse wave and tissue Doppler) and are described below as examples of how assessment of a plurality of signals can guide treatment modalities both acutely and chronically. Referring to FIGS. 2 and 3, one can see how cardiac tissue motion affects myocardial acceleration, velocity and displacement. In FIG. 2, myocardial velocity derived from echocardiographic tissue Doppler (extrinsic) is illustrated (top—longitudinal velocity and bottom—rotational velocity) along with implanted accelerometer derived (intrinsic) data (middle). In FIG. 3, we can see the affect of organized atrial arrhythmia, atrial flutter (AFL'), on tissue Doppler curves (top) compared to velocity time curves in normal sinus rhythm (NSR) (Schecter S, et al. The Effects of Atrial Flutter on Left Ventricular Rotation: A Tissue Doppler Study. Heart Rhythm Society 2005; 2(1S): S134). Similarly derived data from intracardiac accelerometers are able to be analyzed yielding information about tissue motion and potential stroke risk. As atrial arrhythmia becomes more disorganized and tissue motion in the LA and LAA lessens, blood flow in the atria becomes more stagnant with greater risk of clot formation. Any such intrinsically and extrinsically derived signals are acquired and scored along a range of values and entered into algorithms for analysis and determination of risk for stroke or other adverse outcome.

Mitral regurgitation (MR) can precipitate atrial arrhythmias. Regurgitant blood flow across the mitral valve from the left ventricle into the left atrium (as well as tricuspid regurgitation in the right heart) increases atrial pressure, distends the atrial chambers and pulmonary veins and promotes atrial dysrrhythmia. The presence of MR can be diagnosed with a variety of techniques including physical examination (stethoscope, palpation), echocardiography, angiography (extrinsic) or detected intrinsically with cardiac acoustics (intracardiac or extrathoracic). In one aspect of the invention, MR is detected by signals detected from indwelling catheters fit with sensors/transducers that detect MR's effects in the atria and pulmonary veins. These catheters may be permanently implanted or temporarily introduced (e.g. during ablation procedures).

Dysynchrony can precipitate atrial arrhythmias. It is well known in the cardiology literature that atrial-ventricular dysynchrony can increase atrial pressures and promote atrial arrhythmia. Intra-ventricular dysynchrony also increases MR and MR severity can be reduced with CRT. Additionally, CRT therapy has been shown to reduce AF burden and it is not uncommon for patients with chronic AF to convert and maintain normal sinus rhythm (NSR) after a CRT implant. Thus, dysynchrony indices (DI) are valuable physiologic characteristics that help define the pathologic state of atrial arrhythmias as well.

Whether it be MR severity, dysynchrony, cardiac chamber geometry or other characteristic, the degree of severity is characterized along a range or numerical scale based on similarly acquired data gathered from population studies. This graduated scale is more accurately derived with monitoring techniques capable of transmitting such information via wireless telemetry to a central processing center/data bank 1000 and back to the specific monitoring equipment (e.g. implanted device, echocardiography machine, ablation apparatus, separate apparatus) as depicted in FIG. 4 and ultimately processed in 400 and communicated to the operator in 500 via a user interface (e.g. graphical display) or alternate means as will be described in more detail below. The resulting numerically scored data, 210, can then be input to a Characterization Apparatus, 300, in FIG. 1, where comparisons are made and algorithms employed to generate an informational data set that relays the relevant information to the user and/or directs programming of an implanted device or catheter based processor/system (400) as part of a closed loop system. In a preferred embodiment, 400 contains the necessary software and hardware to process the data from multiple sources and can communicate this informational data set to the clinician and/or transmit the information to 500, user interface.

In FIG. 1, at step 110 the data is compiled, and if in analog form, is digitized in 100 and then input to 200 where the physiological descriptors are scored as to characterize the detected pathophysiological features of the patient using multivariate statistical techniques such as Discriminant Analysis. Other statistical techniques may be used to perform an analysis of these physiological descriptors. By way of example, Discriminant Analysis compares measured MR, left atrial geometry (G), pulmonary vein anatomy (G), DI, atrial tissue velocity characteristics (RAA with conventional implanted lead system, LA with CS based accelerometer or LAA with a diagnostic or therapeutic ablation catheter). Values related to these characteristics are assigned a binary numerical value along a range of values based on comparisons to normal template data acquired from population studies. As an example, an arbitrary characteristic A may be defined as a function of intracardiac measurements; left atrial size, (Discriminant characteristic X), average pulmonary vein diameter (Discriminant characteristic Y) and left ventricular mass (Discriminant characteristic Z). Respectively, these characteristics are obtained by extrinsic echocardiography, CT angiography of the atria and pulmonary veins and/or cardiac MRI, accrued and digitized within the Detection Apparatus, 100. In one embodiment, an operator can have the option to review any automatically obtained characteristic before entry into 200, to confirm that adequate data is present for data processing. Analysis apparatus 200 assigns to characteristic A a specific value as described below. The values of A reflect a composite of findings that are weighted based on level of relevance to characteristic A and results of pooled data (i.e., known results of extrinsic diagnostic tests and intrinsic sensor based data) obtained from a large number of patients (this data will have been telemetered to the central processing center and then telemetered back at periodic intervals for updating). Thus, characteristic A may equal a1 when Discriminant characteristics X, Y and Z fall into a specific range of values. The relative importance of Discriminant characteristics X, Y and Z for Characteristic A is represented by values x, y and z. In this example x may be weighted at 50 percent (x=0.50), y and z at 25 percent, and A=a1 when Discriminant value L<=xX+yY+zZ Referring to FIG. 5a, and by way of example, A equal to a2 or a3 is found when the cardiac anatomy is found to be associated with a small to moderate risk (1-5 percent/year) of thomboembolism and stroke, and values in excess of a5 are found when values are consistent with a risk in excess of 8 percent/year risk and regardless of other characteristics, recommendations for anticoagulation are made (dotted line 325). In this case example, values of a4 and a5 are seen under circumstances where risk is between 5 and 8 percent/year (step 330 ensues). The higher the number following a, the more likely the risk of stroke than when the number is smaller. When the risk is less than 1 percent/year (a1), anticoagulation would not be of benefit (step 315 ensues and recommendation for no anticoagulation is made without need to evaluate other variables). Changes in any or all of these characteristics over time can redirect system recommendations and physician treatment. By way of example, remodeling of the heart after aggressive treatment with anti-hypertensive therapy, ablation therapy, mitral valve replacement/repair or CRT implantation may confer a significant reduction in risk and warrant discontinuation of anticoagulation with Warfarin.

Figure 5A:
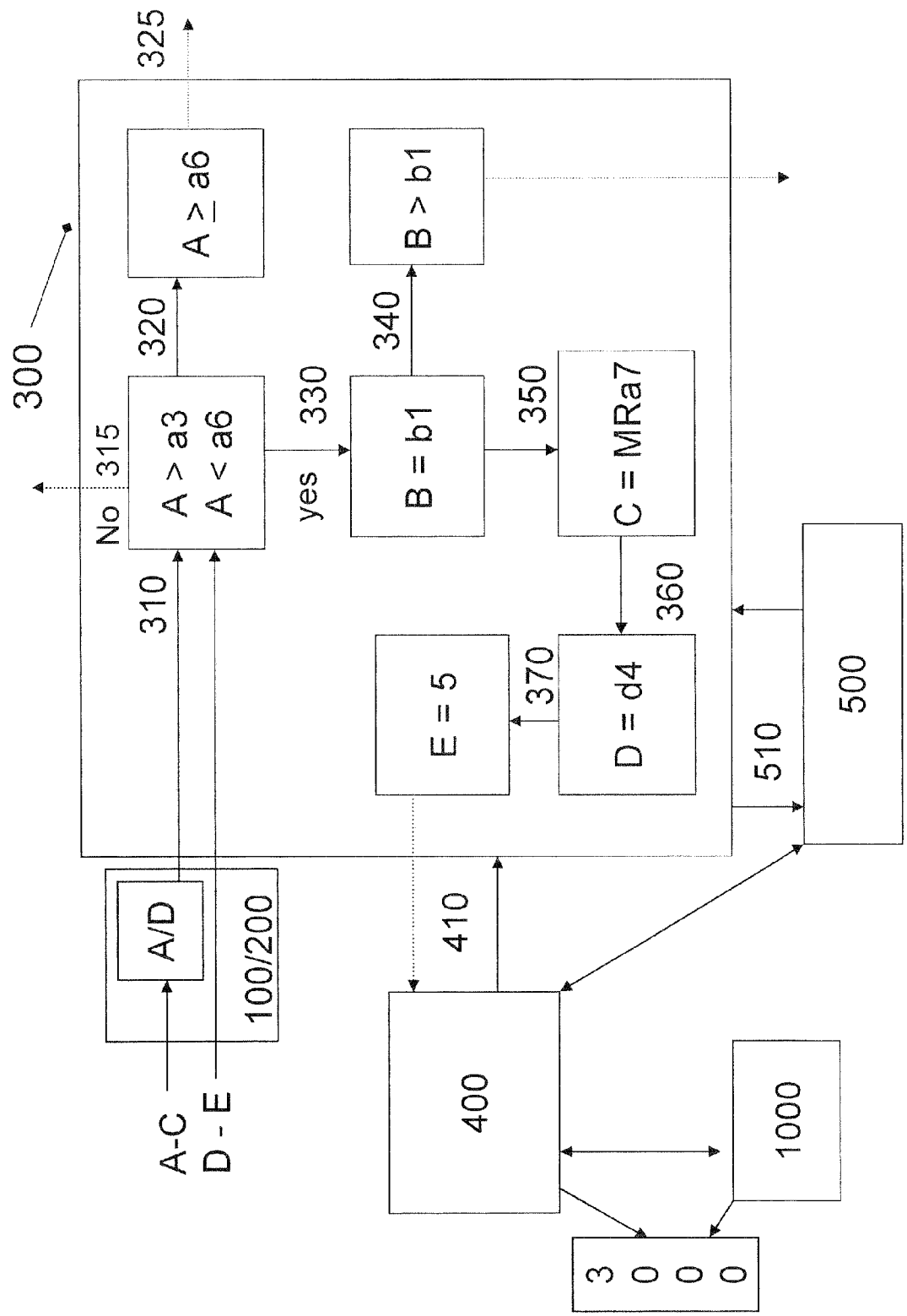
FIG. 5a shows an algorithm written in pseudocode implemented within the Characterization Apparatus 300 of FIG. 1 in accordance with this invention. Dotted arrows indicate specific examples of information data sets/clinical recommendations that are available to the following physician after further processing (e.g. with neural networks) in a device/device programmer or peripherally located processing center, 400 (located within the implanted device, extrinsic imaging equipment or stand alone equipment). Communication and processing of data between 300 and 400 is bi-directional, 410. Communication with a central processing center, 1000, enables system access to population studies/data. Communication of data to an Electronic Medical Record, 3000, and processing in 3000 is also a feature of this invention.

Referring to FIG. 5a, characteristics A through E which have been detected/acquired and if needed digitized in 100 are organized and scored based on comparisons to template data in 200 after comparisons to pooled data at the CPC. These scored characteristics are then entered into Characterization Apparatus 300. For purposes of explanation, we will denote physiological properties A as anatomic/geometric characteristics, B as the hematologic profile, C as mitral valve characteristics, D as a DI and E as properties of tissue motion, though other properties can be included and those mentioned herein are purely exemplary. If needed, physiological properties are digitized (A/D) and the resulting data is input to A at step 310. Characteristics A through E are a numerical value along a graduated scale or can reflect the absence or presence of a specific condition (0 or 1). A is an anatomic/geometry index as described above. In this particular example, the geometric findings alone are consistent with a moderately elevated risk of stroke. Thus, the derived anatomic/geometry index, A, will fall within a preset range of values, a4-a5. If the risk was felt to be marked (e.g. LA size>6 cm), A>=a6, step 325 would ensue and recommendations for anticoagulation would be made without need to consider other physiologic variables. At periodic intervals this evaluation is performed and the resulting data is stored and available for review at follow up visits or in a preferred embodiment by wireless telemetry. The frequency of such periodic evaluations can be a default value or programmable time interval (e.g. every day) or every time invasive testing (e.g. angiography, electrophysiology studies) or an imaging modality is performed (e.g. cardiac MRI, echocardiography). Likewise, the pooled data from the central processing center, 1000, is able to be communicated back to the implanted device or external diagnostic equipment at periodic intervals (e.g. every month), as more data is entered from patients/equipment with access to this technology (FIG. 4). In this case example, the patient has a moderately increased risk for stroke based on chamber size/geometry at query box A and, the algorithm proceeds to step 330. Without additional data this would prompt the system to recommend anti-coagulation therapy, though other factors may be considered if available and demonstrate that, in fact, stroke risk is quite low. Thus, the more data input into the system the more accurate the predictor algorithms will be. The range of values for A are determined from pooled data acquired from numerous patients who have access to this technology and outcome analysis based on univariate statistical data of similar patients (e.g. age/sex matched) treated with or without anti-coagulation. The predictive power of the algorithm increases as more characteristics are input and more complex statistical analyses will be required (e.g. multivariate analysis). By analysis of multiple patient subgroups, the recommendations made by the algorithm will be more predictive of outcome (i.e. risk:benefit ratio of any given therapy) than existing guidelines that are based on broad patient categories (*Circulation.* 2001; 104:2118) evaluated in large clinical trials (e.g. SPAF trial).

Characteristic B relates more specifically to hematologic profiles. Numerous laboratory tests can be performed and help prognosticate a given patient's risk for clotting and are well known in the medical literature (e.g. bleeding time, platelet aggregate factors, concentration of coagulation factors). In query box B, the patient is found to have a hematologic profile that confers significant protection against clotting (value=b1) and step 350 ensues to the next step as to evaluate valvular function, C. If the risk were greater a different analysis would occur at 340.

In this case example, C is equal to MRa (step 360 ensues) when Discriminant Analysis of echocardiographic data demonstrate that the MR is severe and flow exceeds a certain value and flows retrograde into the pulmonary veins and LAA. The direction of MR can be detected based on extrinsic echocardiographic imaging and noted to be eccentric rather than central. Such a finding is also consistent with electromechanical dysynchrony and when taken in context of other DI variables (e.g. sinus bradycardia, first degree AV block and intraventricular dysynchrony) at D, step 370 follows as such a patient will likely respond to CRT.

Again the value of C is assigned in Analysis Apparatus 200 and can specifically denote properties of MR. In 200 the degree of MR is given a value (MRa7) based on comparisons of MR severity derived from normal and abnormal patients along a graduated scale. Thus, in this particular patient, echocardiographic assessment of MR determines that it is severe (e.g. EROA value near maximal) and the value of MR is graded numerically as 7 out of 10, where 10 is most severe and 0 being normal with no MR present. The fact that the patient has severe MR that effectively increases blood flow in the atria and LAA reduces the risk for clot formation and stroke despite a high atrial fibrillation burden.

Note that in this case the specific algorithm employed applies to patients with persistent of near persistent atrial fibrillation (>80% AF burden). Other, albeit similar, algorithms are applied when AF burden is less. AF burden is able to be defined by an implanted device that records episodes of atrial arrhythmias (intrinsically derived) or alternatively based on known frequency of atrial arrhythmias noted on outpatient monitoring. AF burden may be defined by the percentage of time a given patient is in AF rather than in NSR (>80 percent if sampled data in this example). Conventional pacing systems implanted today routinely provide such data to clinicians at time of device follow-up, but, this data alone is insufficient to guide treatment, especially if limited episodes of paroxysmal AF are detected. Alternatively. AF burden can be an integral part of the flow diagram in FIG. 5*a*, rather than having the system implement separate flow diagrams for specific degrees of AF burden.

Returning to FIG. 5*a*, step 370 ensues, and at query box E, the patient is labeled as someone with high atrial tissue velocity and LAA blood flow velocities based on a composite of echocardiographic and even catheter based acceleration indices. The composite of all this data is communicated to the clinician in any format. By way of example, when the values of A, B, C, D, E fall within a specific range, a message is communicated in display box 500: "this patient has been identified as one who will have a positive outcome from cardiac resynchronization therapy and a low risk for thromboembolism and stroke (<2%). Based on patients with similar clinical findings, this patient's prognosis will improve with CRT implantation and reassessment of need for mitral valve surgery should be made after CRT. This patient will have a high likelihood of maintaining sinus rhythm and placement of an atrial lead as part of the CRT device is recommended (note that patients with chronic atrial fibrillation may not always have an atrial lead implant which slightly increases procedural risk). Long-term anticoagulation may have an unfavorable risk:benefit ratio and should be re-evaluated after CT implantation. Individual outcomes may vary."

In this case example, the patient is labeled as having a value in the CPC of a4, b1, MRa7, d4, e5. For a patient with an AF burden of less than 20 percent the recommendations and statistical analyses as described above hold true. If a patient with the same characteristics had an AF burden of different value (e.g. >50%), a different set of recommendations would be made. Thus, several different algorithms may be applied with the same variables with different clinical outcomes. An implanted device that records AF burden will utilize different algorithms at 300 dependent on the AF burden. Multiple algorithms which examine the same set of variables can exist for patients with varying degrees of AF burden (e.g. intervals of 5%).

Alternatively or additionally, the system can simply report percentage risk and likelihood of response based on statistical analysis of the individual patient's characteristics as compared to that of other patients who have had data entered into the CPC with known outcome under different treatment strategies (present statistical data). The former implements neural networks in order to have higher level functioning (see below) and a more sophisticated means of communication in written language, whereas the latter simply reports known statistical facts. Certain advantages and disadvantages exist for either approach (e.g. medical-legal considerations).

Neural Networks

Figure 5B:
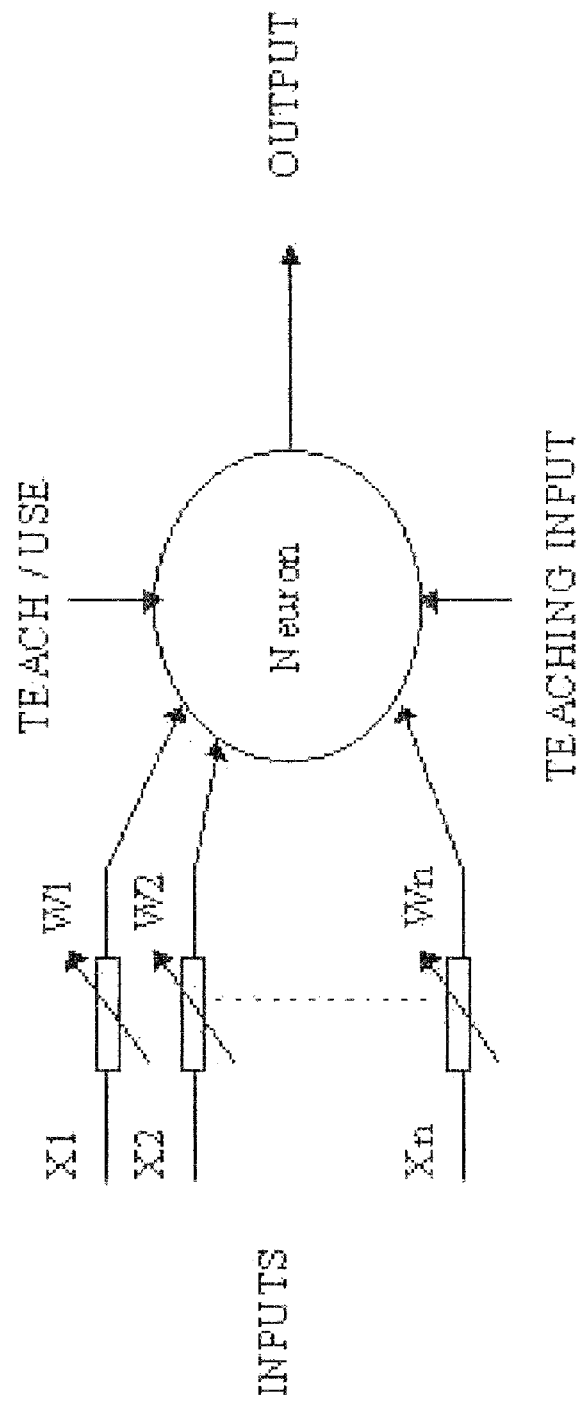
FIG. 5b illustrates how neural networks are applied in accordance with the invention.

Implementation of artificial neural networks (ANN) will allow sensor fusion by combining values of several different sensor derived indices. Sensor fusion will enable the system to learn complex relationships among individual sensor values which would otherwise be lost if the values are individually analyzed. ANN is used in this case example for predicting risk of thromboembolism and stroke and will guide decision making about which patients should be committed to long-term anticoagulation. The McCulloch and Pitts model (MCP) for ANN allows for the inputs to be 'weighted', thus the effect that each input has at decision making is dependent on the weight of the particular input. The weight of an input is a number which when multiplied with the input gives the weighted input. These weighted inputs are then added together and if they exceed a pre-set threshold value, the neuron fires. In any other case the neuron does not fire. In this example, the output is the recommendation for anticoagulation with Warfarin or not. Referring to FIG. 5b, we see how an MCP neuron is implemented. Variables x1-x3 are input and weighted before input to the Neuron. Teaching or training is accomplished with outcome data from the CPC, under differing physiologic conditions. In a more complex ANN, the teaching can also be used to determine the weighting, W1-3, of each input.

In mathematical terms, the neuron fires (recommendation for anticoagulation) if and only if;

$$X1W1+X2W2+X3W3+\ldots >Q$$

The addition of input weights and of the threshold makes this neuron a very flexible and powerful one. The MCP neuron has the ability to adapt to a particular situation by changing its weights and/or threshold. Various algorithms exist that cause the neuron to 'adapt'; (e.g. the Delta rule and the back error propagation) are known by those experienced in the art. The former is used in feed-forward networks and the latter in feedback networks.

Generalization of the neuron gives the neuron a sense of similarity under similar physiologic states and enables it to respond 'sensibly' to patterns not seen due to incomplete training up until the time a large database is collected at the CPC and telecommunicated back to the peripheral/internal processing system 400.

The ability of the system to generate such data is dependent on existing data sets/statistical probabilities of outcome (prognostic information) with different permutations of parameters (e.g. A-E) that are compared in 1000 (FIG. 4) to findings in other patients who's outcome has been determined and stored in the CPC. Neural networks are applied in 400 and/or 1000 to update and 'teach' the system at periodic intervals from data made available from open connectivity with the CPC.

In our particular case example, after CRT, changes in the parameters may or may not still indicate that the patient would benefit from anticoagulation or mitral valve surgery. Post-operative assessment of intrinsic device based indices (e.g. AF burden) in conjunction with extrinsic imaging techniques is used to determine further management. In a preferred embodiment, the extrinsic and intrinsic data acquired can be analyzed in a complementary fashion, compared to previous case examples with similar findings in the central processing center and the system can provide the clinician with statistical data detailing expected response rates and prognosis (e.g. with and without mitral valve surgery and anticoagulation).

Apparatus predictor algorithms may not rely on a single index but may incorporate redundancy techniques as to improve specificity much in the same way an operator may define hypokinetic myocardium if such findings are found in more than one imaging plane on a conventional two dimensional echocardiogram. This is also important as inadequate data quality or the lack of specific sensors/data may compromise the systems ability to define certain characteristics. Thus, the system can rely on a plurality of signals, intrinsic and/or extrinsic in its analysis. This case is by way of an example and illustrates how any number of redundant or repetitive steps occurs with fast software algorithms.

In the example described herein this patient is defined as someone likely to respond to CRT. This result can be output in any format (digital or analog), numeric or as written language. Neural networks or comparable means can analyze the available data, draw comparisons between the individual case and a library/data bank of other cases stored in the central processing center with outcome information prior to reporting any observations and before making recommendations. The apparatus/algorithms may specifically report such characteristics via a graphical display and/or printed out by monitor/printer or other user interface, 500, as described above. 500 can represent any method of communication to the clinician. This will allow an operator to review and manually input data based on subjective assessment of the acquired data (step 510) before final processing in 300 (FIG. 2). Such data may be transmitted by removable media such as hard drives or magnetic-optical discs or via wireless telemetry to 1000, the CPC, as well as, in a preferred embodiment, to an electronic medical record, EMR, at 3000. In an alternate embodiment, processing in 400 occurs where the EMR is generated and processed.

As the current invention allows for acquisition of data acquired from large population studies with entry of the data into a central data bank, the algorithms employed and recommendations generated (IDS) apply evidence-based medicine. Initially, such technology will be used for monitoring purposes and record keeping in an EMR. As more patients have access to equipment with such technologic capability, the more predictive the IDS will be for determining prognosis. Once validated with large scale clinical trials of patient subgroups as defined by the algorithm described herein, formal recommendations are relayed to the practitioner based on the predictor algorithms described.

It is readily apparent that such a technologic advancement holds promise to reduce health care costs and improve patient outcome as patients most likely to benefit from specific therapies will undergo such treatment and those patients unlikely to benefit from specific therapies will avoid the potential risks/health care costs of such treatment and adverse outcome (e.g. prolonged hospital stays and operative complications). This data is made available to certain governing bodies (AMA FDA) and even health insurance companies. Availability of such data to health insurance companies should be with patient consent. Incentives to patients to participate in such programs such as a guaranteed reduction in insurance premiums will promote better medical care for the individual and society at large. Insurance companies may be better able to define risk of adverse outcome and improve patient compliance with recommended treatments. Such a system will help drive down health care costs. Patients who consent to have insurance companies access such data can have their implanted device programmed to communicate this data to a specific processing center via wireless telemetry or other means.

Health Care System Communication

For example, the implanted device can be programmed to communicate to a CPC at a given bandwidth and communicate to health care providers at an alternate frequency. This is illustrated in FIG. 6. Switch A within the internal processing unit of an implanted device, 400*d*, allows open communication to the CPC and switch B allows open communication to a given health care provider (HCP). Alternatively, removable media from a device programmer can be downloaded and sent to HCP at periodic intervals.

In addition to open communication with non-physician providers/governmental bodies, the system can alert the following physician and other providers that specific testing need to be updated (FIG. 6, step 550). By way of example, a patient who has an implanted prosthetic heart valve should undergo echocardiographic evaluations at periodic intervals (e.g. annually) or a patient with mitral regurgitation should be evaluated every two years. As the system is updated when such testing is performed, it can have pre-specified time-outs if such testing has not been performed after a given timeframe. Thus, the time frame can be set by the physician (e.g. within the implanted device) and a reminder generated by the device at the appropriate time via the device programmer or wireless communication to the clinician's office (e.g. EMR 3000). If the system detects a change in condition, more frequent reminders can be generated and communicated to the following physician, overriding the default, pre-programmed time-outs. Guidelines made by medical societies such as the American Heart Association (e.g. in cooperation with health care providers/insurers) can be used to set default time-outs for specific clinical scenarios. These may be modified/updated by the system when changes in patient status occur or guidelines change based on new statistical data generated by the CPC. Such changes in guidelines for test frequency can be based on any univariate analysis or multivariate analysis of a plurality of intrinsically or extrinsically derived data.

Outcome analysis performed within the device and/or a central processing center gathers and processes such data via wireless telemetry from extrinsic diagnostic equipment and/or implanted devices with such capability. Thus, at pre-programmed intervals such intrinsically and extrinsically derived data sends acquired data in numeric format (e.g. characteristics A-E) to the central processing center (FIG. 4) and from the central processing center back to 400 within the implanted devices/device programmers, extrinsic diagnostic equipment and/or EMR (double headed arrows in FIG. 4).

Any and all data received by the central processing center (CPC) is stored in a data bank, and tracked for all patients who have such data entered. The data can be from implanted devices (intrinsic) or external diagnostic equipment (extrinsic). Patient specific therapies and outcome are input to the CPC. The outcome data can be in the form of any index of cardiac performance or hard endpoints such as morbidity or mortality data. The data is processed via neural networks or other technique in 1000, 3000 and/or 400 with the output data being any recommendations for patient treatment communicated to the user in 500 (e.g. recommendation for valve replacement) as is illustrated in FIG. 5a, Translation Function As described in the parent application, the data acquired by implanted accelerometers is processed to derive measurements related to LV rotation/motion/displacement consistent with tissue velocity data and is evaluated and compared to analogous extrinsically acquired data. Such data is communicated via device-device communication (e.g. echocardiography and CRT device programmer) either with removable media or other interface (e.g. Bluetooth), or if needed, by manual entry of intrinsically and extrinsically acquired data sets (e.g. results from controlled studies).

Methods for deriving velocity or displacement data from accelerometers using integrator circuits are known in the art and described in detail in referenced U.S. Pat. No. 5,549,650 (Bornzin et al.) and are applicable to the concepts described. Physiological properties that are input to the Analysis Apparatus may be both extrinsically derived and derived from a plurality of signals within the implanted device and used for comparative purposes. The use of accelerometers and other lead based sensor measurements (e.g. impedance data) described herein are merely exemplary and any sensor or transducer which is part of an implanted device can acquire data that is incorporated into these algorithms. As more data is acquired from multiple patients with access to such technology (e.g. implanted CRT devices possessing these features), the comparisons between intrinsic and extrinsic diagnostic modalities are used to formulate a translation function that converts various intrinsic indices to extrinsic indices and vice versa. This is described in the parent application but will be discussed herein as it applies to defining the pathologic state of atrial arrhythmias and the effect of atrial arrhythmia on cardiac performance.

Figure 19:
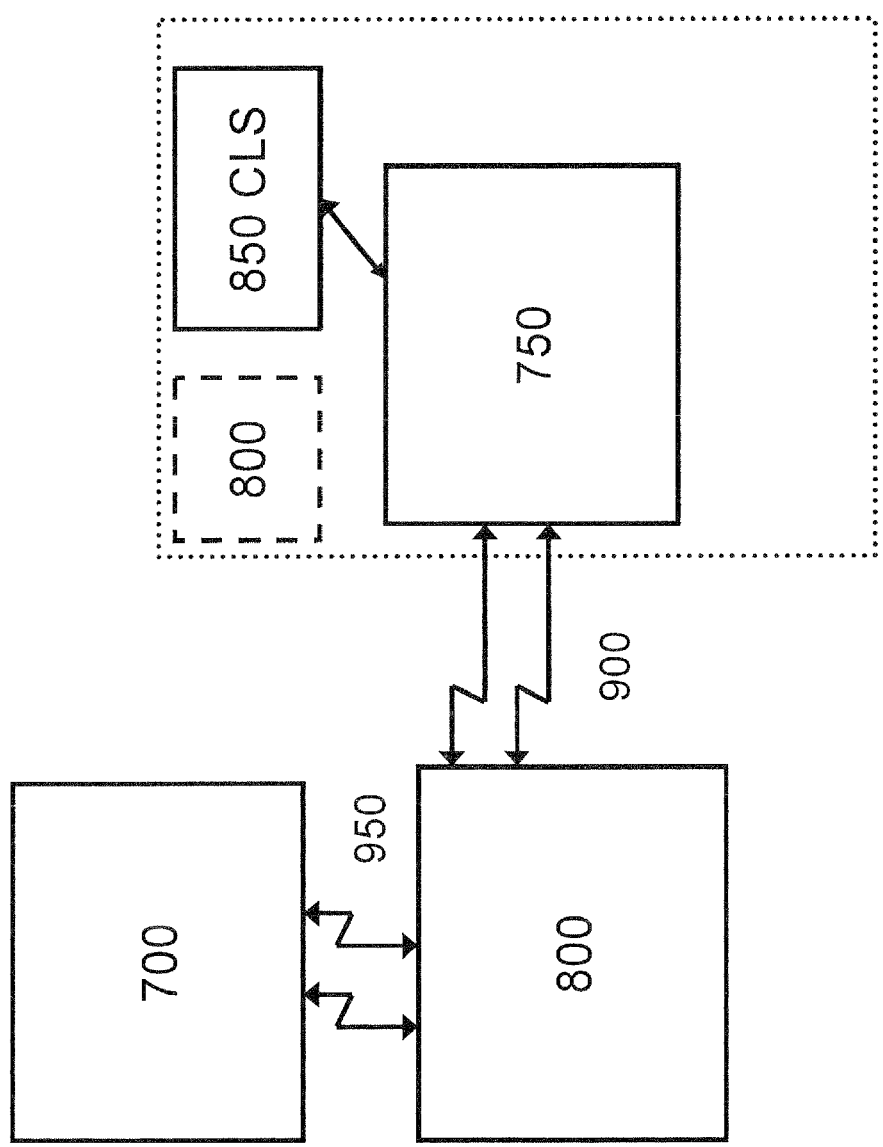
FIG. 19 illustrates how an intrinsic/extrinsic comparison apparatus function. 700 is any extrinsic apparatus such as an echocardiography machine. 750 is an intrinsic apparatus such as an implanted CRM device or catheter based system inserted into the patient for diagnostic/therapeutic purposes. 800 is the intrinsic/extrinsic apparatus that can be an integral part of an implanted device (dotted lined box) or a separate apparatus (solid line box). 850 represents a closed loop system that can be within an implanted device or other diagnostic/therapeutic equipment (e.g. ablation catheter apparatus). 900 and 950 is bi-directional wireless telemetry.

As described in the parent patent application, when this invention is applied to indwelling catheters (e.g. CRM device leads), mathematical methods for correlating the various indices (e.g. regression analysis) are used as to allow translation of device based data to imaging based data and vice versa and calibrate one methodologies measurements to the other. Novel mathematical units or unitless indices that are assigned a value along a graduated scale can apply to both intrinsically and extrinsically derived data. These units are derived as to develop a universal mathematical language that is applicable to both device-based and non-device based sensors/transducers. The translation function is generated from within apparatus 300 or from a separate apparatus as described below (FIG. 19).

A translation function in a more simplified approach is used to translate mathematical units derived from one type of implanted sensor into conventionally recognized units. For example, displacement data derived from lead based accelerometers to indices used with tissue Doppler or speckle tracking techniques (e.g. longitudinal mm distance, radians rotated). This can be defined for an individual patient based on simultaneously acquired data with, for example, echocardiography and catheter based accelerometers by using a look up table developed from pooled data (registry) derived from numerous patients who have had both intrinsic and extrinsic data measured. Regression analysis or other technique is used to correlate any intrinsically and extrinsically derived index (FIG. 7) such as an accelerometer derived index of LAA tissue displacement (ordinate) expressed in volts or microamperes and echocardiographic derived index of LAA tissue velocity (abscissa) described in cm/sec. Functions/equations are then derived that translate an intrinsic index to an extrinsic index and vice versa. The equations described herein are merely exemplary and may be linear, exponential, non-linear etc.

Figure 12:
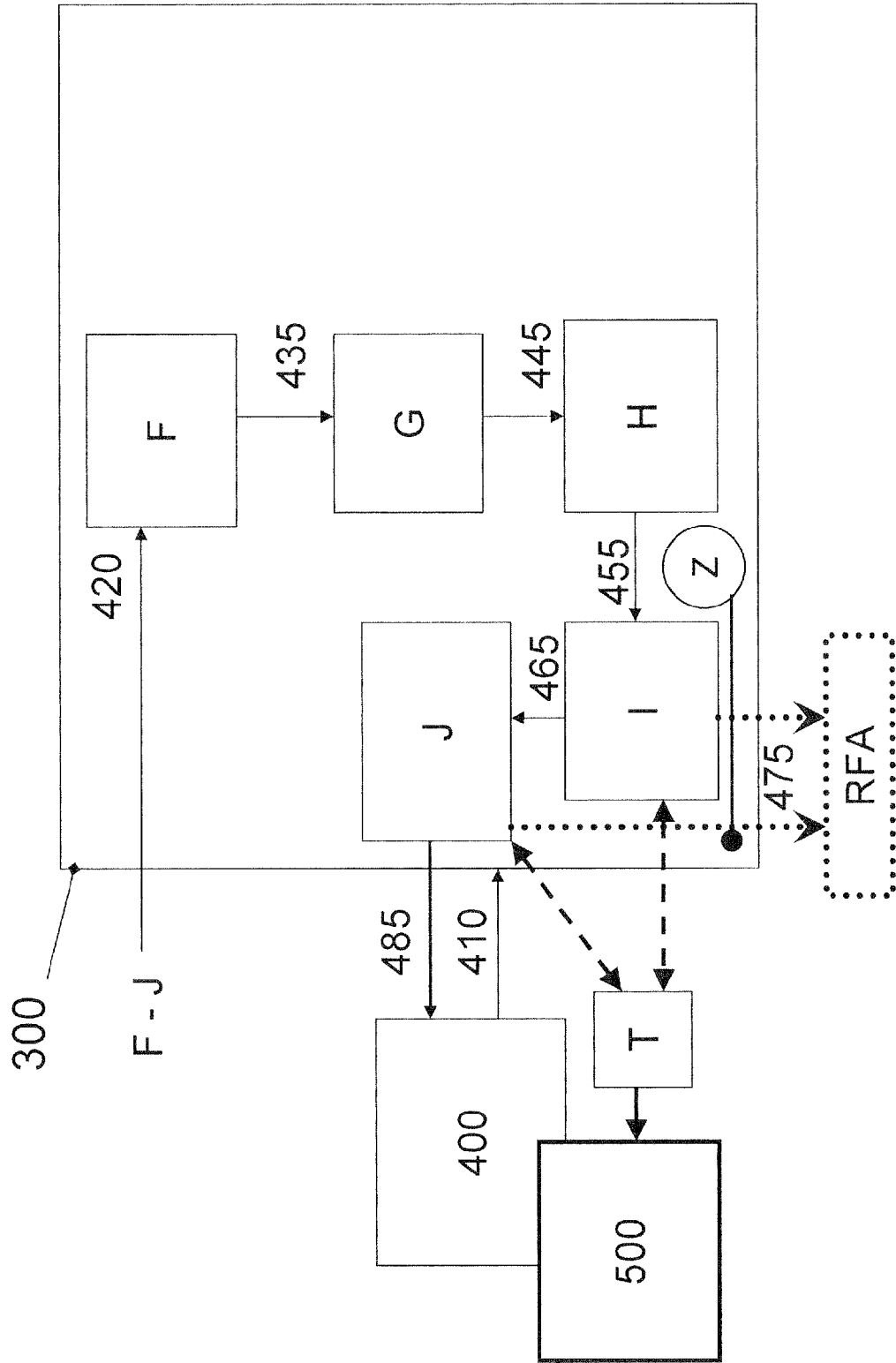
FIG. 12 details an algorithm written in pseudo-code within the Characterization Apparatus 300 as a block diagram characterizing cardiac performance as it relates to atrial arrhythmias. These data are sent via wireless telemetry to a central processing center (CPC) along with outcome information in all patients who have access to this technology and then communicated back to the clinician as to guide treatment or communicated back to an implanted device or other apparatus integrated into closed loop control systems. In this example, the apparatus is comprised of a temporarily implanted ablation catheter, RFA, and serves to assist the operator in performing a pulmonary vein isolation procedure, preferably in a semi-automatic fashion using robotic instrumentation.

A common metric is defined that corresponds to both or either intrinsic and extrinsic units of expression. In this example, a percentage index denoted the LAA motion index ranges between $<=0.10$ and $>=0.90$. Patients with normal LAA motion (e.g. NSR without pathology) have values of LAA tissue velocity (cm/sec) and accelerometer derived current (uA) that are greater than a certain value (e.g. >40 cm/sec, >10 uA, respectively). If both or either conditions are met, the LAA motion index is set to be $>=0.90$. The physiologic descriptor for LAA motion is valued at 0.90. Thus, for LAA motion (derived intrinsically via an accelerometer and/or extrinsically via echocardiographic tissue Doppler) a unitless, universal mathematical index is defined. This numerical value is entered into the software algorithms described as detailed more below for physiologic descriptors I and J (FIG. 12). Note that this invention allows for motion indices to be derived for different cardiac structures (e.g. mitral annulus, myocardial regions) and the LAA motion index is exemplary. In the parent application motion of myocardial regions of interest were described.

In this example, a linear equation is defined that correlates the amperage generated from an accelerometer from displacement related to atrial appendage motion to cm/sec tissue velocity derived from tissue Doppler. Such a conversion can utilize single integration of acquired acceleration measurements so that both extrinsic and intrinsically acquired data are in units of cm/sec. Double integration may be used to derive units of displacement. In one application of the invention, extrinsically derived (echocardiography) tissue Doppler measurements of acceleration, velocity and displacement are correlated with accelerometer based measurements of the same. A closest fit polynomial equation is derived that serves to translate one data set to the other, thereby drawing a relationship of tissue motion properties gathered by extrinsically and intrinsically derived means. Again, calibration of one methodology (e.g. intrinsic/accelerometer acquired measurements) is based on the other (e.g. extrinsic/tissue Doppler).

Such an equation may be patient specific (i.e. based on comparison of data derived from one patient's TEE and implanted accelerometer data) or based on data compiled from multiple patients with access to this technology. In this simplified example, the relationship is defined as LAA (cm/sec)=k*Acc (uA). k=10. In other patients k may equal a different value, though when pooled data is accrued and averaged, k will be assigned a default value that will be suitable for any individual patient when comparisons between extrinsically and intrinsically acquired data sets are not available (i.e. patient does not have echocardiographic data but only implanted sensor data). As TEE and accelerometer derived data were acquired, averaged and compared in this patient, this relationship is defined. In other patients who may not have had a TEE performed, an equation based on pooled data from other patients who have had both procedures performed can be implemented. Thus, the translation function can be applied in an individual or inferred from data acquired and stored (CPC) from patient sub-groups even without the need to obtain extrinsic or intrinsic data sets but only one data set whereby the analogous data set is inferred.

Figure 10:
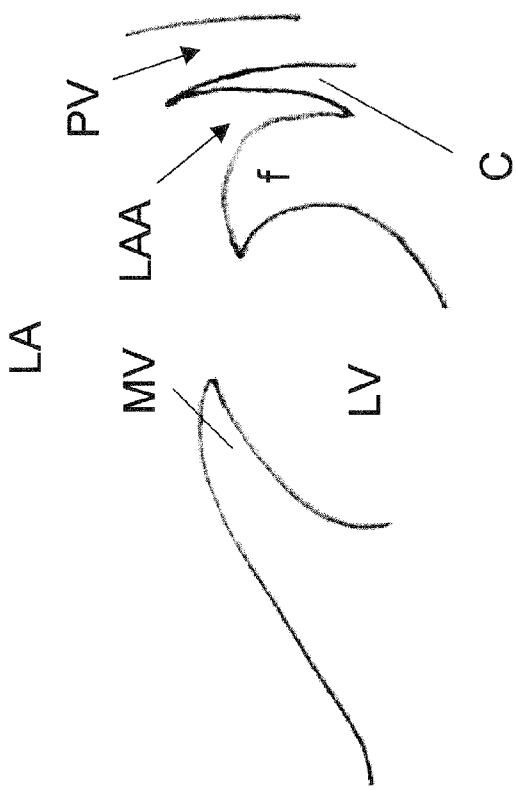
FIG. 10a demonstrates how echo derived tissue displacement (middle) obtained with tissue tracking or speckle tracking is analogous to accelerometer derived displacement (bottom) with a region of interest in the left atrial appendage (LAA); (ECG—top).
FIG. 10b demonstrates the anatomy of the LAA and PV and their proximity and common wall, C.
FIG. 10c illustrates how wall motion is affected as the catheter tip moves between the LAA and PV.

To further elaborate on the concepts described, the reader is referred to FIG. 8. FIG. 8 illustrates how displacement of myocardium from base to apex is derived from evaluation of Doppler derived tissue velocity as a function of time (integration of curve). This data is obtained from lead based accelerometer signals in an analogous fashion (see parent application) with displacement data derived with two integrator circuits (Bornzin et al., U.S. Pat. No. 5,549,650). Use of one integrator circuit will derive tissue velocity data. These techniques are known in the art and are described in the referenced patent by Bornzin. In FIG. 10*a* it can be appreciated that echocardiographic displacement of LAA tissue (e.g. wave A) and other variable amplitude waves are directly proportionate to displacement measured with an accelerometer (e.g. acc A). Note, that for this example, accelerometer deformation is possible in two degrees of freedom (above and below the baseline) and such directionality is ascribed numerically and graphically. An omni-directional transducer will allow the system to function in three dimensional space as will be described in more detail below. The amount of current generated with an accelerometer type sensor/transducer and the reported displacement index derived is calibrated and referenced to displacement measured by tissue Doppler echocardiography (e.g. the average displacement of multiple AF waves over one or more cardiac cycles) and the corresponding average displacement of accelerometer waves. These averages can then be used to generate line D in FIG. 7.

Risk Assessment for Stroke

Figure 11:
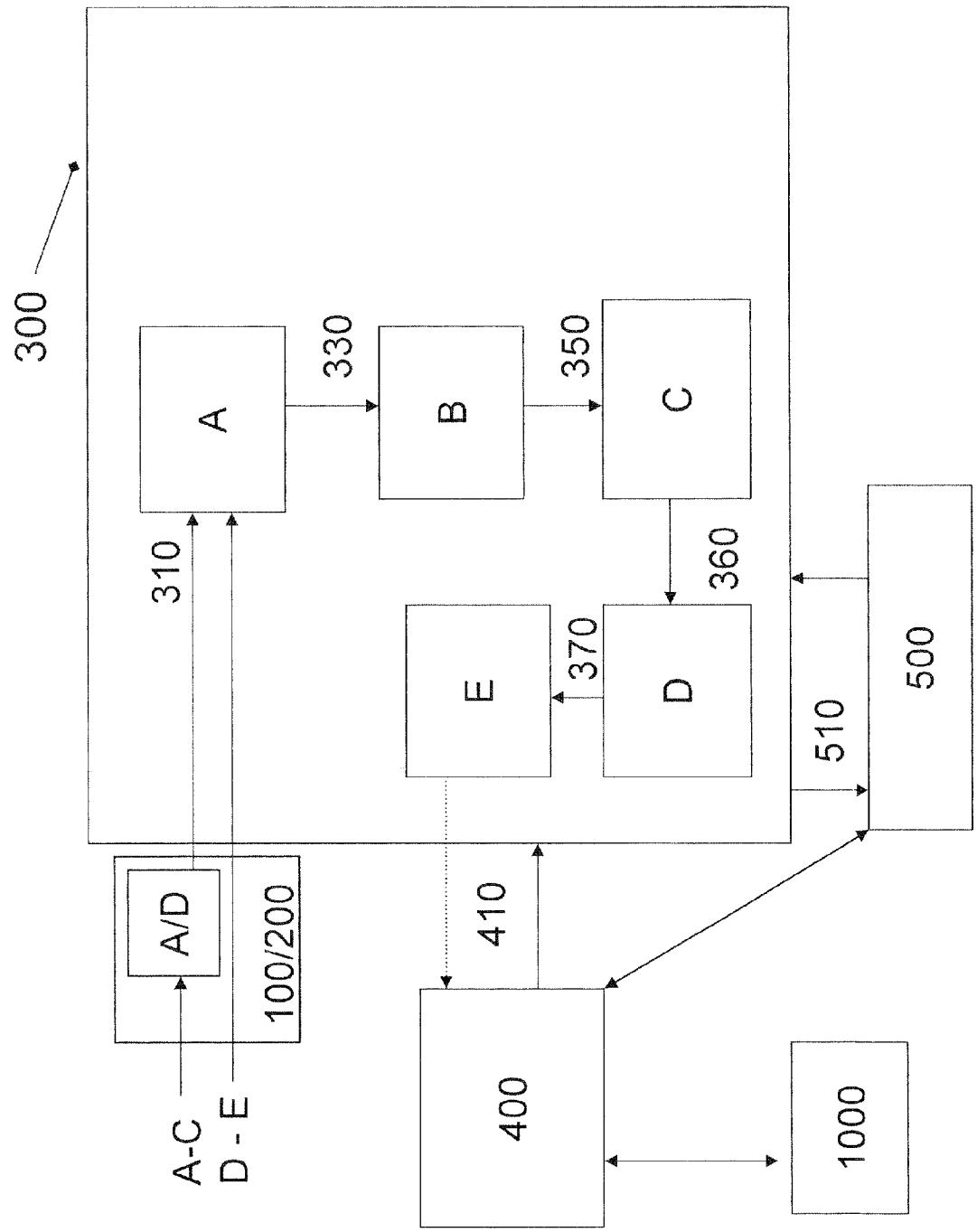
FIG. 11 details an algorithm written in pseudo-code within the Characterization Apparatus 300 as a block diagram characterizing cardiac structure and function as it relates to a variety of pathologic traits that effect atrial cardiac performance. These data are sent via wireless telemetry to a central processing center (CPC) along with outcome information in all patients who have access to this technology which is then communicated back to the clinician as to guide treatment or communicated back to an implanted device or other apparatus integrated into closed loop control systems.

In one application of the translation function, the acquired data is implemented for determining risk of thromboembolism, stroke, and the likelihood of response to certain therapeutic modalities as is described in the case example below and illustrated in FIG. 11 (similar to FIG. 5*a*).

In this case example, we can denote physiologic characteristic A as a description of extrinsically derived anatomic reconstruction of the left atrium from any imaging modality or modalities (e.g. MRI, CT angiography, echo) and B-C as extrinsically derived properties related to the left atrium and LAA based on echocardiography. D and E are intrinsically derived signals derived from either a permanently or temporarily implanted catheter in or juxtaposed to the right and/or left atrium and surrounding structures (e.g. pulmonary veins, atrial appendages). Note that either analog or digital signals may be acquired dependent on the transducer and equipment used to acquire the signals. Such a catheter may be part of an implanted lead system for a CRM device or a catheter used for monitoring electro-mechanical properties of atrial tissue and delivering therapy (e.g. ablation catheter). In this example, characteristic A comprises different measurements including chamber sizes (Discriminant characteristic X), various anatomic classes of the confluence between the pulmonary veins (Discriminant characteristic Y) and left atrial appendage (Discriminant characteristic Z) or other descriptor of atrial anatomy. Those experienced in the art of pulmonary vein ablation for treatment of atrial fibrillation will recognize that these parameters can be analyzed and compared in large groups of patients for determination of risk:benefit ratio of a patient having ablation therapy for AF over other therapy (e.g. anti-arrhythmic agents) and to even direct procedural technique and predict procedural success.

Thus, A relates to the anatomic, geometric structure of the LA, LAA and surrounding structures such as the pulmonary veins (PV), inter-atrial septum (IAS), or even the mitral valve (MV). B relates to characteristics of blood flow (A wave magnitude, E/A wave ratio), and C describes characteristics of left atrial appendage blood flow (frequency, mean amplitude). D describes the temporal characteristics of catheter-derived motion (derived by a lead based accelerometer or permanently implanted atrial lead) such as the relationship to ventricular depolarization, and frequency of motion. E relates to the amplitude of any motion detected by such a catheter. B through E can be further characterized with Discriminant characteristics as described for A. Higher frequency, lower amplitude motion that is not temporally related to ventricular depolarization will confer a higher risk for thrombus formation. In this case example, characteristics A through E are assigned specific values and entered into 300 as depicted in the flow diagram in FIG. 11.

The system provides information that is prognostic and guides decision-making about whether or not to perform a procedure (e.g. AF ablation) and defines risk for thromboembolism and stroke, especially when combined with lead based accelerometer data and other data acquired from an implanted CRM device. The system also is capable of providing guidance for performing therapeutic procedures (e.g. ablation technique). The latter will be described in more detail below with reference letters F-J in FIG. 12.

System Application to Ablation Therapy

Non-invasive, extrinsically acquired data about atrial anatomy are implemented during AF ablation as to guide the delivery of radiofrequency energy. CT angiographic anatomic maps are superimposed upon electroanatomic maps generated by the location of the ablation catheter tip. The electroanatomic maps utilize an electroanatomic-magnetic mapping system in a fashion similar to navigational systems and are well known in the art. Such navigational systems that have been developed and are currently available are manufactured by CARTO (Biosense-Webster), NavX (Endocardial Solutions, St. Paul, Minn., USA), LocaLisa (Medtronic, Minneapolis, Minn., USA). The details of these technologies can be found in current Electrophysiology textbooks and the references cited above. Algorithms using the technologies described herein are implemented to improve the precision and safety of ablation therapy. These algorithms can be open or closed loop. In a preferred application of the invention the software algorithms described herein are implemented in robotic systems for performing ablation. This will reduce and potentially eliminate operator exposure to fluoroscopy.

In FIG. 12, physiologic descriptors F-J are input to Characterization Apparatus 300. These descriptors are acquired before and/or during an ablation procedure. F and G are representative of atrial anatomy and the relationship of the ablation catheter to the pulmonary vein os and surrounding structures. F is derived from CT angiography and G from electroanatomic mapping. In an alternate embodiment, F and G are acquired from an intracardiac tactile exploration system, as will be described below. Thus, ablation should be only possible if the catheter tip is in the appropriate location (e.g. around the pulmonary vein openings). If the catheter is deep within a pulmonary vein, ablation will not be possible (reduces the risk of pulmonary vein stenosis). H is representative of intracardiac electrical signals as derived by computerized multichannel recording systems well known in the practice of Electrophysiology (e.g. EP Med Systems Inc., Mt. Arlington, N.J.) and the appropriate mapping catheter systems (e.g. Lasso, Biosense-Webster, Diamond Bar, Calif., USA). These signals provide the operator with information about where the catheter tip is, as well as, whether or not electrical isolation of any pulmonary vein has been accomplished. Thus, if specific intracardiac signals originating from within the pulmonary vein are detected, ablation can occur. Once these signals are no longer present, ablation cannot occur. Examples of these local depolarization signals or intracardiac electrograms are provided within the references noted above and are understood by those experienced in the art. Thus, in this example, characterization of anatomic location and regional depolarization triggers on and off switches at step 435, 445 and 455 that either allow or disallow ablation energy from being delivered (i.e. with a closed loop system). These switches can be inactivated or reversed by the operator by input commands at 410 after review of transmitted data via 485 to a display or other apparatus at 500 and effectuate an open loop system.

Figure 13:
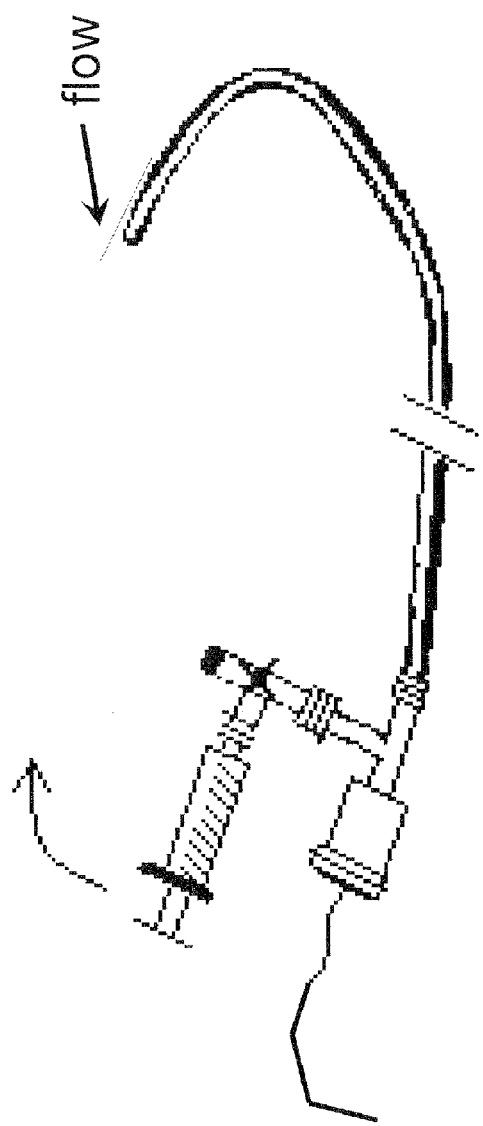
FIG. 13 illustrates an ablation catheter capable of transmitting and receiving ultrasound signals (e.g. Doppler flowire).
Figure 14:
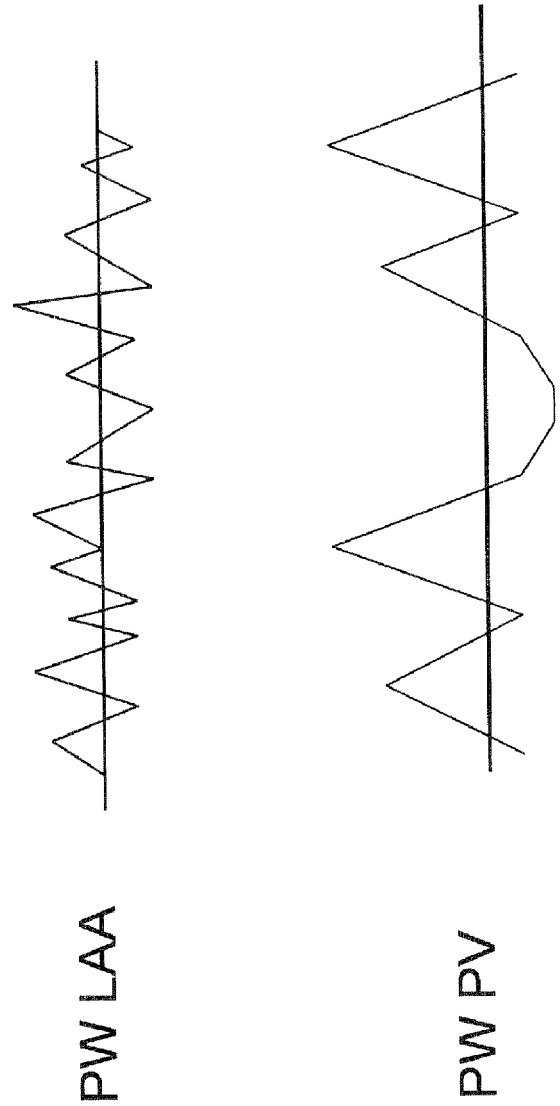
FIG. 14 shows signals derived from echocardiography equipment (top) with a region of interest in the LAA (tissue Doppler or pulse-wave Doppler) and within the os of the pulmonary vein, PV (bottom).

I is representative of echocardiographic determinations of intracardiac blood flow velocities. More specifically, it is comprised of Discriminant characteristics that detail extrinsically derived measurements of LAA pulse wave Doppler of LAA blood flow (FIG. 14). Such data are acquired before and/or during the procedure with transesophageal or even intracardiac echocardiography (e.g. Acunav, Siemens, Medical, Mountain View, Calif., USA) performed at the time of ablation. In one mode of the invention, such an intracardiac Doppler ultrasound transducer is incorporated into the ablation catheter rendering the catheter itself capable of transmitting and receiving intracardiac Doppler ultrasound (FIG. 13). This transducer can be as simple as a Doppler flowire (flow in Figure) similar to those used during coronary interventions for detection of hemodynamcally significant stenoses and investigated by the author early in the development of such technology (Guiding Catheters with Side Holes Relieve Pressure Damping and Improve Coronary Blood Flow Assessment with the Doppler Flowire. Schecter et. al. Circulation 1994; 90: 4, part 2: 1-164). More complex or alternate transducers/sensors may be incorporated into the catheter system and can include acoustic sensors and accelerometers or other type of sensor capable of detecting tissue motion and blood flow (intracardiac tactile exploration system) as will be described below. The manufacturing of conventional ablation catheters is well known in the art and such a design can implement catheters similar to those developed by Celsius Thermocool, Biosense-Webster in conjunction with transducers/sensors that detect blood flow, tissue motion and sound using accelerometer technology.

In one embodiment, the echocardiographic data (e.g. transesophageal, intracardiac ultrasound) is compared to catheter acquired measurements of intracardiac assessment of LAA and PV blood flow (e.g. catheter fitted with a Doppler Flowire) as to derive an individualized translation function appropriate for the specific individual rather than one that is based on data acquired from large patient subgroups (FIG. 14). The echocardiographic procedure can be done before or during data acquisition from catheter based sensors/transducers. In FIG. 12, such a translation function is derived in T from data obtained at J and I (double headed arrows).

The amplitude and frequency of the derived signal pulsed wave Doppler blood flow from the LAA (top) and PV (bottom) can be appreciated in FIG. 14. The LAA is most proximate to the left upper pulmonary vein (LUPV). This anatomic relationship is illustrated in FIG. 10b. During ablation near the LUPV, the ablation catheter can inadvertently enter the LAA and cause perforation and cardiac tamponade with cardiovascular collapse. Additionally, having the catheter in this region can increase the risk of thrombus formation and stroke.

The precise anatomic location of the ablation catheter may be obscure and inaccurately portrayed despite assessment of CT angiographic data, electroanatomic mapping techniques and intracardiac electrogram recordings. Thus, the additional data related to PV and LAA blood flow (e.g. intracardiac Doppler flowire) or tissue motion will improve procedural success and reduce risk when combined with other data. As is demonstrated in FIG. 14, LAA blood flow has higher frequency, lower amplitude signals than pulmonary venous flow. These identifiable characteristics of blood flow are shared in general and are used to identify where the catheter is located, though more subtle variations may occur depending on the presenting heart rhythm, as well as, an individual patient's physiology and anatomy. The exact location of the catheter tip cannot be defined with 2 or 3 dimensional echocardiography alone secondary to a number of factors including acoustic shadowing, attenuation, echo-reflectivity. These limitations will not be a factor when measuring blood flow characteristics. Additionally, the introduction of additional hardware/catheters increases procedural times and risk. Thus, this system provides a surrogate for accurately determining where the catheter tip is located using blood flow Doppler techniques, while conventional or even intracardiac echocardiography will be more limited. The ability to detect tissue motion using tissue Doppler techniques or in a preferred embodiment with accelerometer generated signals or in an alternate embodiment with an intracardiac tactile exploration system will further refine the system's capabilities as described below.

Characteristic motion of the LAA during AF differs from other atrial tissue. Even at the juncture between the left upper pulmonary vein (LUPV) and LAA one will see rapid signal damping and attenuation (FIG. 10c—arrow on bottom) secondary to signal attenuation due to the common wall and transverse sinus which is a pericardial reflection situated between the LUPV and LAA (FIG. 10b). In FIG. 10c (top) one sees the amplitude of tissue velocity at the LAA free wall (f in FIG. 10b) is significantly greater than the LAA-PV common wall (bottom-left FIG. 10c) and is significantly damped when the region of interest is on the wall of the pulmonary vein (PV) as demonstrated in 10c (bottom-right). As the region sampled is moved from an area with significant wall motion (LAA) to one without wall motion (PV), an abrupt change in signal intensity/frequency is noted which help the operator localize, with confidence, the LAA and pulmonary veins for a variety of procedures.

By way of example, a lead designed to be situated in the extracardiac space (e.g. epicardial via a limited thoracotomy) is located in a prime vantage point near the PVs and LAA. The advantages of this include performance of ablation from an extracardiac approach (e.g. intra-operative pulmonary vein isolation during open heart surgery), localization and implantation of extra-cardiac (e.g. epicardial) LA pacing electrodes, and delivery of anti-tachycardia pacing and low energy, painless cardioversion for the maintenance of normal sinus rhythm. During placement of a lead based accelerometer (manufactured along with one or more of electrodes for pacing, sensing, defibrillation), the operator can confirm appropriate localization of the lead with such technology as surgical implant techniques are generally performed with limited visualization (e.g. via mini-thoracotomy).

System Application to Ablation Therapy—Catheter Design

Figure 15:
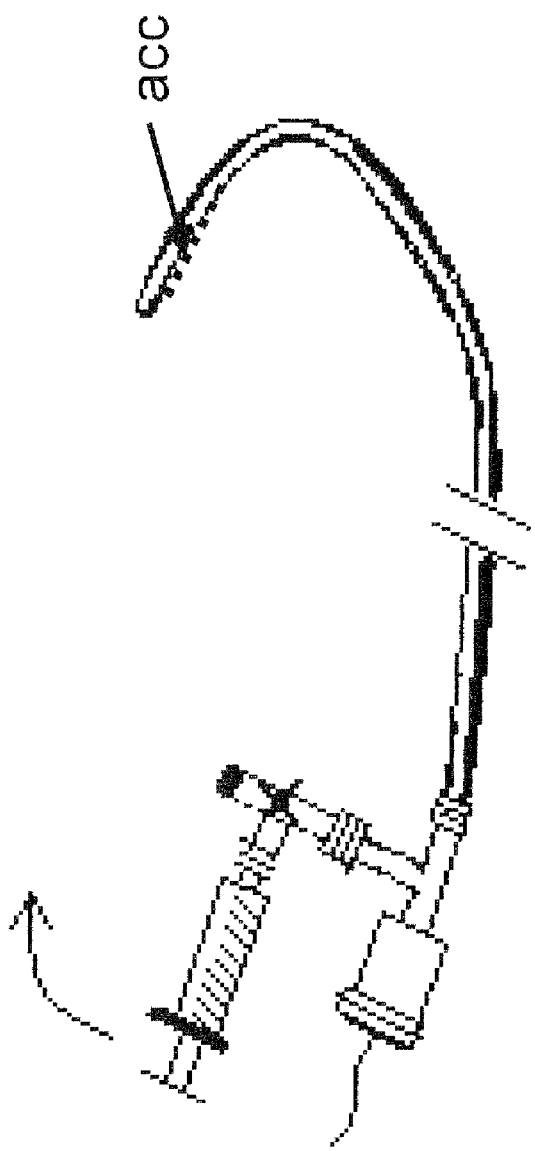
FIG. 15 illustrates an ablation catheter or other catheter (outer catheter) used for performing transeptal puncture fitted with a piezoelectric transducer (acc) as to obtain the waveforms illustrated in FIG. 14.

In a preferred mode of the invention, the ablation catheter tip itself can detect wall motion using accelerometer type technology similar to that described in the example with NPIT, in the parent application, and ultrasound technology will not be necessary. Thus in FIG. 12, at J, catheter based determinations of wall motion are evaluated. The design of catheters capable of radiofrequency ablation is well known in the art (Celsius Thermocool, Biosense-Webster). The catheter design required to accomplish ablation and detect wall motion requires a lead based accelerometer (or comparable mechanical sensor) near the tip of the catheter as illustrated in FIG. 15. Any piezoelectric material known by those experienced in the art, piez, suitable for design of an accelerometer, is coupled to the catheter and generates voltage, and thus, current of adequate amplitude that is proportionate to degree of deformation. The addition of an accelerometer to the catheter system should not significantly affect the size, diameter or material characteristics of the catheter (e.g. maneuverability). The accelerometer can be uni-axial or preferably multi-axial if the latter design does not affect catheter properties. Lead based accelerometers are also known in the art and are described in the disclosed patent application by Bornzin, as well as the other references provided. The novel feature of this catheter is that it can function in both capacities and the system can derive indices of tissue motion analogous those obtained with tissue Doppler/speckle tracking echocardiography via the translation function as will be described in more detail below.

Referring to FIG. 12, if at J, wall motion is consistent with that of the LAA (laa in FIG. 10), an alarm is triggered and/or ablation therapy prevented. If, on the other hand, wall motion is not characteristic of the LAA (pv in FIG. 10), ablation therapy (RFA) is enabled at 475. If such a catheter is not available then step 465 does not occur and step 475 occurs. At step 485 this data is communicated to the processor, 400, for final analysis (e.g. neural networks) and to the operator where it may be reviewed via 500 (e.g. digital image display). At step 410 the operator can input information into the system if needed. Communication at 500 can occur via written language, graphical display of the characteristic waveforms or other technique. Confirming the location of the catheter tip is not only important for precise localization but also to confirm adequate contact with tissue. Tissue contact is necessary for ablation to be effective and it is generally thought that unsuccessful procedures are in large part due to incomplete tissue contact.

As the operator is usually viewing the fluoroscopic location of the catheters and display data derived from CT angiography and electro-anatomic mapping, it may be difficult for him or her to look at additional visual information. Thus, the inventor has devised a novel means for communicating data representative of wall motion to the operator at 500 as will be described below.

Tactile Feedback System

Additionally or alternatively, 485 can transmit data that is appreciated within the catheter itself. Uni-directional or in a preferable mode of the invention, omni-directional vibration/displacement of the catheter tip detected by a catheter based accelerometer (or other sensor such as a Doppler flowire) is transmitted to the handle of the catheter. Conventional ablation catheter handles known in the art have a means for deforming and changing the shape of the catheter tip. Such handles can also accommodate a tactile feedback motor with shaft and offset weight mounted as a component within the catheter handle for providing vibration/displacement to the hand of the operator. The vibration/displacement simulates the motion detected by the intracardiac accelerometer at J and such simulation is optimized using the translation function, T, in FIG. 12 as it applies to tissue Doppler or speckle tracking echocardiographic quantification of such motion at I and accelerometer based quantification of motion as described above. Thus, the fine, high frequency motion of the LAA is translated into a similar quality motion in the catheter handle (FIG. 16).

Such a tactile feedback mechanism will allow the operator to detect the high frequency signal generated from accelerated bubble formation. Detection of this phenomenon will reduce risk of tissue necrosis and perforation.

This innovation will require A/D conversion of the catheter derived accelerometer signal and then D/A conversion within the catheter handle (or other connected apparatus) to generate the tactile feedback system. The hardware and software for the tactile feedback system may be in the handle or, in a preferred embodiment, in a separate apparatus that is connected to the catheter handle (FIG. 16). The latter is the preferred mode of the invention as it will reduce the bulk and weight of the catheter handle. The intensity of the tactile feedback motor is adjustable as some operators may desire a more subtle sensation than other operators. Telemetry capabilities are present within such a handle and/or separate apparatus and allows for wireless transfer/communication of data with other equipment and the CPC.

Figure 16:
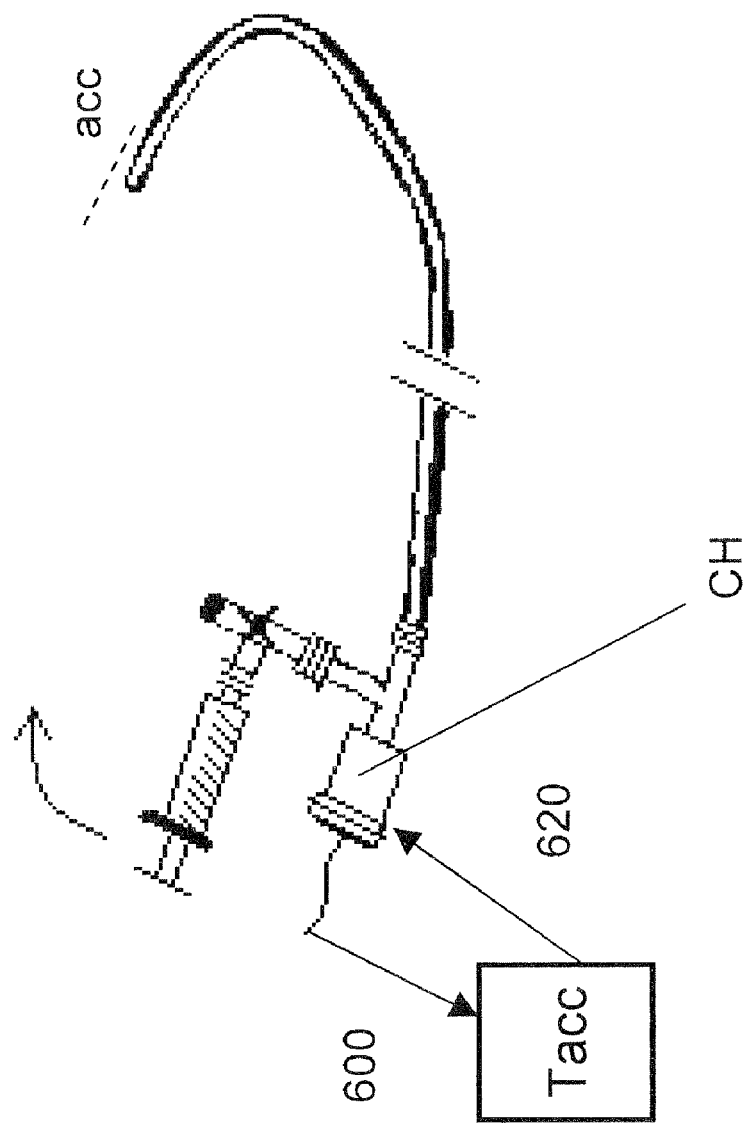
FIG. 16 demonstrates an ablation catheter handle with tactile feedback system. At 600 the current generated from an accelerometer at the catheter tip is presented to Tacc where the current amplitude is A/D converted (translation function) as to derive a numerical score proportionate to the degree of catheter tip deformation and then D/A converted to generate a current at 620 that drives the tactile feedback system within the catheter handle CH. The degree of motion/vibration of the catheter handle. CH, is proportionate to the original degree of deformation/motion of the catheter tip. The translation function is implemented to determine the range of values.

FIG. 16 demonstrates an ablation catheter handle with tactile feedback system, CH. Via 600 the voltage (or current based on fixed impedance within the system, e.g. conductor 600) generated from an accelerometer at the catheter tip is presented to Tacc where the current amplitude is A/D converted as to derive a numerical score proportionate to the degree of catheter tip deformation and then D/A converted to generate a current at 620 that drives the tactile feedback system within the catheter handle CH. The degree of motion/vibration of the catheter handle, CH, is proportionate to the original degree of deformation/motion of the catheter tip and thus current amplitude in 600 and 620. The translation function is implemented to determine the range of values.

The inventor believes that the most pleasing and physiologic relevant motion imparted to the catheter handle is a to and fro sensation along the axis of the catheter handle itself. Thus, the motion imparted to the operator via the tactile feedback system is one where the handle subtly moves forward and backward along its central longitudinal axis without actual movement of the catheter itself. The frequency and amplitude of motion is proportionate to that of the catheter tip housing the accelerometer and, in a preferred embodiment, determined with the translation function. The tactile feedback system, however, does not necessitate the translation function to be operational for any individual patient. Ideally, the actual design of the catheter itself, and relationship of deformation/motion of the catheter to that of the tactile feedback system relies on analysis of the correlation between intracardiac tissue motion and accelerometer motion as described herein. This represents the best mode for recreating the tactile sensation of intracardiac tissue motion, though alternate and simplified design schemes that do not necessitate a correlation between signals are within the scope and spirit of the invention.

In order to provide the closest simulation of the reaction of the catheter tip to the intracardiac environment, the inventor design of the catheter handle incorporates a dampening system. The dampening system allows a buffer between operator manipulation of the catheter and actual tissue contact. In addition to the elastic properties of the catheter itself, a dampening system, Damp in FIG. 17e, (e.g. spring loaded mechanism) within the catheter handle is constructed as part of the feedback motor and shaft/offset weight. When the degree of deformation of piez (p in FIG. 17d) relative to the force generated at the catheter handle becomes non-linear and asymptotic (f in FIG. 17d), the dampening system will provide a buffer as to reduce the likelihood of cardiac perforation. An alarm can be triggered as to notify the operator that such a condition has been met (asterisk in FIG. 17d).

Acoustic Feedback System

In an alternate embodiment, 500, produces an audible tone of variable frequency that is proportionate to the detected intracardiac/vibration. The sound generated can be modified to be more acoustically pleasing by either stepping down or up the frequency by a specific number of octaves. Audible signals commonly implemented with intracardiac Doppler are reproduced and communicated to the operator in a similar fashion to conventional echocardiography equipment. Such a feature will have the most accurate representation of cardiac physiology by implementing the translation function after comparisons are made between extrinsically (e.g. transthoracic echocardiography) and intrinsically derived signals (e.g. intracardiac catheter based Doppler). Lead based accelerometers may be designed and implemented to detect vibration related to sound, rather than wall motion or both sound and wall motion. For such a feature, signal processing techniques are used (e.g. band pass filters) and catheter designs implemented that specifically allow the piezoelectric transducer to resonate at frequencies similar to those generated from intracardiac blood flow and valvular effects (acoustic impedance matching) for detection of sound (can be in addition to transducers designed to detect wall motion).

Free floating vibration dependent transducers within the intracardiac chambers are implemented to acquire acoustical data and transducers opposed to myocardial tissue for acquisition of motion data. Directionality of sound is determined based on catheter location (i.e. electroanatomic mapping) and a virtual intracardiac experience (VIE) created by reproducing cardiac sounds in three-dimensional space using surround sound technology known in the audio video industry (e.g. Dolby Surround 5.1). If, for example, a catheter is positioned such that the mitral valve is lateral and aortic valve anterior to the catheter tip while the PVs are posteriorly located, the sound field can produce the characteristic acoustics of PV blood flow behind the operator, aortic valve anterior to the operator and mitral flow to the left. As changes in catheter position occur, the sound field is modified accordingly. The closer the transducer is to a given source the louder the sound. Thus, the operator can most accurately determine catheter position and intracardiac wall contact by using a number of sensory experiences and a plurality of signals. Tactile, auditory and visual input will improve procedural success.

This virtual intracardiac experience (VIE) where the operator can experience visual, auditory and tactile sensations will improve procedural success and provide insights into cardiac properties never before appreciated. This VIE is better realized if intrinsically derived tactile stimuli are acquired as described below.

Intracardiac Tactile Exploration System (ITES)

In an alternate embodiment, a virtual intracardiac reconstruction is based on intrinsically acquired tactile stimuli. The inventor has designed an intracardiac tactile exploration system that provides the operator with a morphologic image of the intracardiac environment (Murphy System) and ultimately can replace the need for CT angiography and electroanatomic mapping systems. In this mode of the invention, biomimetically engineered whiskers capable of tactile perception are incorporated into the distal end of the intracardiac catheter (FIG. 17f), similar to the vibrissae of several species of terrestrial and marine mammals used to sense and navigate environment (Kaneko M, Kanayama N, Tsuji T. Active Antenna for Contact Sensing. IEEE Transactions on Robotics and Automation, Vol. 14, No 2, April 1998. 278-291). In these species, the bending moment at the whisker base is used to generate a three dimensional spatial representation related to shape and fluid flow, for example, in rats and seals, respectively (Neimark M A, Andermann M L, Hopfield J J, Moore C I. Vibrissa resonance as a Transduction Mechanism for Tactile Encoding. J Neurosci, Jul. 23, 2003. 23(16): 6499-6509) (Hartmann M J, Johnson N J, Towal R B, Assad C. Mechanical Characteristics of Rat Vibrissae: Resonant Frequencies and Damping in Isolated Whiskers and in the Awake Behaving Animal. J Neurosci, Jul. 23, 2003. 23(16): 6510-6519). In the animal model, the vibrissal array functions as to accurately gauge aperture width (Krup D J, Matell M S, Brisben A J, Oliveira L M, Nicolelis M A L. Behavioral Properties of the Trigeminal Somatosensory System in Rats Performing Whicker-Dependent Tactile Discriminations. J Neurosci, Aug. 1, 2001, 21(15): 5752-5763. In the complex environment of the atria, an accurate representation of aperture width (e.g. atrial appendage and pulmonary veins) will improve procedural success.

In order to simulate the animal model, spring-steel wire or plastic polymer whiskers ae fitted with strain-gauges (SG) at the base for measurement of at least two orthogonal components of moment (Solomon J H, Hartmann M J. Robotic whiskers used to sense features. Nature 2006, vol 443, 525). Analysis of moments of each whisker using four radial contact points in space will enable extraction of information about object shape and fluid flow properties if whisker construct has adequate elasticity to be deformed from fluid flow.

Figure 17A:
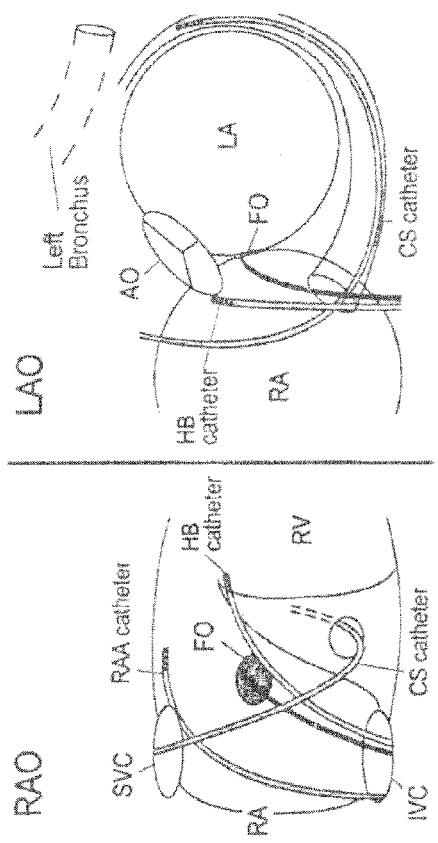
FIG. 17a illustrates how a transeptal puncture is performed.
Figure 17B:
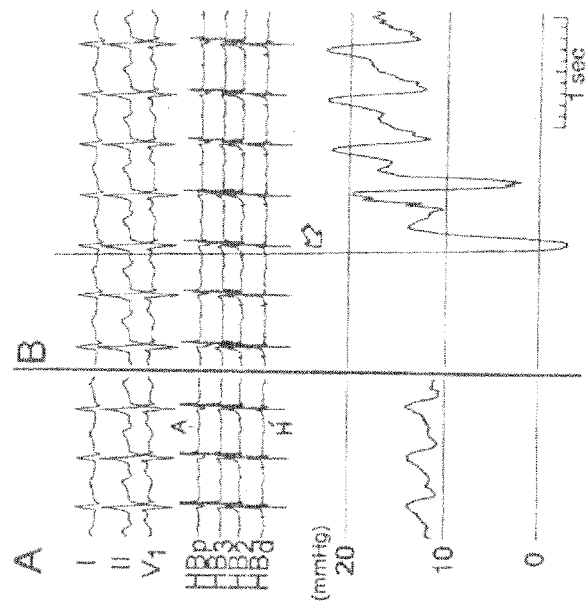
FIG. 17b demonstrates how intracardiac pressures change as the catheter traverses the IAS between the RA and LA. Note how manometry data is lost for a number of cardiac cycles during the transeptal puncture and the exact location of the catheter tip is unknown. Tactile feedback from a piezoelectric transducer will provide the operator with sensory information indicative of the pressure transmitted to the catheter tip and thus the location on the catheter tip.
Figure 17C:
FIG. 17c illustrates how a Brokenbrough needle including piezoelectric material in its distal most portion can act as an accelerometer in accordance with the invention.

Modification of the sheath design to accommodate additional whiskers will improve the tactile representation of the intracardiac environment. Thus, this invention is not limited to any specific number or arrangement of whiskers. By way of example, four additional whiskers are positioned on the inner portion of the catheter, in between the locations of circumferentially located whiskers in an alternating arrangement. In this design each whisker will be separated from the next by 45 degrees and by a distance equal to the radial thickness of the sheath, $d_r$ (FIG. 17g). This design simulates that of species with whiskers by adding a specific depth between each row of whiskers.

The strain gauges (SG in FIG. 17f) implemented need to be miniaturized as to fit within the catheter tip. Preferably, such miniaturization is accomplished using nanotechnology. The whiskers are oriented about the circumference of the catheter tip or sheath with the ablation electrodes located centrally (FIG. 17f). In one construct, the ablation apparatus (RFA) is controlled and deployable by the operator from within the catheter sheath (double headed arrows in 170 when needed. Thus, the anatomic reconstruction of the atrium's morphology is acquired using the intracardiac tactile exploration system and once mapping is complete, ablation therapy is delivered. Use of a plurality of data/signals, such as simultaneous electroanatomic mapping, CT angiographic images and intracardiac electrograms, will improve procedural success and cross-verify the data acquired by any individual modality.

Ultimately, the input of CT angiography and mapping data will effectively train the system through the use of neural networks (FIG. 5b) and the translation function described herein as to develop an intracardiac tactile exploration system (ITES) that does not require additional modalities. Comparison between the different modalities in a CPC and bi-directional communication of such data will expedite system training. Thus, in a preferred embodiment, pooled data from the CPC is an integral part of the ITES design as is open connectivity, the translation function and use of neural networks. Predictor-corrector algorithms utilizing extrinsically acquired image data (e.g. CT angiography, electroanatomic mapping) and data sets descriptive of known anatomic variants may be applied to improve the reconstruction of the intracardiac anatomy when needed.

The intracardiac tactile exploration system will reduce costs, minimize fluoroscopic exposure and eliminate the risk of administering intravenous contrast. Referring to FIG. 12, query boxes F, G and I can be replaced by W that is representative of the data acquired by the intracardiac tactile exploration system.

In one embodiment, the spring-steel wire whiskers are also used as electrodes to perform mapping and are constructed of an alloy with piezoelectric properties that allow acquisition of tissue motion as described above. Thus, in this embodiment the whiskers have three components; conductivity for acquisition of intracardiac electrograms, piezoelectric properties for acquisition of tissue acceleration/motion, and contact sensing for recreation of the intracardiac anatomy/geometry. Output signals within SG in FIG. 17f will include these components which are then communicated to the operator, for example, as described above (e.g. tactile feedback system within the catheter handle).

Defining Catheter Location

If an ongoing arrhythmia (i.e. atrial fibrillation) is detected by any of the above modalities (e.g. echocardiographic techniques, catheter based accelerometer, ITES), the translation function of the system described above is enabled to calibrate the amplitude of the transmitted vibration/imparted motion to the catheter handle to be directly proportional to the detected wall motion or pulse-waved Doppler of atrial appendage blood flow (e.g. FIGS. 7 and 10) based on a given individual patient's data and/or in combination with pooled data from the CPC. In either case, the acquired data is collected from either an individual patient or numerous patients in the CPC and a specific translation function is applied during the ablation procedure. The amplitude of such a signal is significantly less or null once wall motion away from the LAA is detected (e.g. transition from laa to pv in FIG. 10). This additional sensory input will assist the operator by confirming the location of the catheter tip and may be applied to other catheter based procedures such as permanent implantation of leads in or about the heart and cardiac chambers (confirm that placement of an intravascular or extra-vascular lead is juxtaposed to atrial or ventricular tissue). For example, such technology will assist placement of leads via a limited thoracotomy approach or alternate minimally invasive approach onto left atrial tissue when visualization is limited.

During an ablation procedure, the additional data set acquired from an accelerometer/ITES will improve procedural success, especially if omni-directional data is acquired (e.g. omnidirectional accelerometer). Four-dimensional tactile sensation (three dimensional motion as a function of time) is then ideally generated from the within the catheter handle, and coupled with electroanatomic mapping and CT angiographic data provides the operator with a virtual intracardiac reconstruction. The operator will be able to appreciate how tissue motion changes as the catheter tip is manipulated in three dimensions. Tissue contact will be better confirmed with tactile feedback.

In one mode of the invention, changes in the impedance measured between two proximate electrodes at the catheter tip can further confirm adequate tissue contact. In FIG. 12, decreases in impedance measurements determined at Z will support that the catheter tip has adequate tissue contact before ablation therapy is delivered at RFA. Marked increases in impedance will also prevent RFA from occurring as this is indicative of tissue injury, inadequate tissue contact or even perforation. Such a feature will provide a fail-safe mechanism if the system were to function autonomously as a closed loop (e.g. robotically) and is depicted by the thick dashed line (switch) emanating from Z in FIG. 12.

In an alternate embodiment of the invention these software algorithms and closed loop system for performing RFA are incorporated into the design of robotic systems that at least semi-automatically perform ablation procedures with minimal operator involvement. The tactile feedback feature/design make this invention most suitable for robotic systems. By way of example, use of electroanatomic mapping systems will allow navigation of the catheter tip to be in close proximity to the os of the pulmonary veins. The tactile feedback system can more specifically direct a robotic system when to deliver ablation energy. Once the characteristic motion is detected (appropriate frequency and amplitude) and partial dampening of the signal is confirmed, adequate tissue contact is occurring. Ablation energy is then delivered while impedance monitoring is occurring and evaluation of intracardiac electrograms is ongoing (e.g. document electrical isolation) as described above. Thus, the algorithm depicted in FIG. 12 is ideal for being incorporated into a semi-automatic robotic system for performing ablation.

If the catheter tip is free floating and not opposed to tissue, no significant impulse is manifested in the catheter handle (though the affect of intracardiac blood flow during the cardiac cycle may generate a subtle, characteristic signal). This will help the operator know when he or she is not in contact with tissue. It is believed by the inventor that the operator will be able to learn to appreciate the sensation of blood flow, tactile characteristics of traversing the interatrial septum or even properties of valvular structures (e.g. mitral valve leaflets, chordae tendinae) through the tactile feedback mechanism. This will be especially true once the system is properly calibrated using the translation function. However, the translation function may not be necessary for the application of such technology. The need for the translation function will be less as more data is complied in the CPC (i.e. an appropriate range of offset/displacement values for the tactile feedback system is established). The invention will enable the operator to appreciate catheter location as characteristic changes in tactile sensation will occur as an ablation catheter is manipulated from an intracavitary space (e.g. LA) to being in light contact with tissue (e.g. PV—fine, low amplitude signal) and then to being adequately opposed to tissue (signal damping). If the catheter is within the LAA a coarser, higher amplitude signal will be appreciated as depicted in FIG. 10c (top compared to bottom waveforms). This technology will improve the operator's ability to manipulate the catheter to be in contact with the appropriate tissue during ablation or during other procedures (e.g. catheter occlusion of the LAA, percutaneous mitral valve repair).

Additionally, once a pulmonary vein isolation procedure is complete specific regions of myocardial tissue may still have disorganized motion and technically be fibrillating even though surface electrocardiograms demonstrate normal sinus rhythm. The presence of and amount of electrically isolated tissue that is fibrillating is relevant to risk of thrombus formation and is entered into the algorithms described such that patients with large regions of atrial tissue with disorganized motion are placed on anticoagulation and not treated as someone with normal sinus rhythm.

Transeptal Puncture

Figure 17:
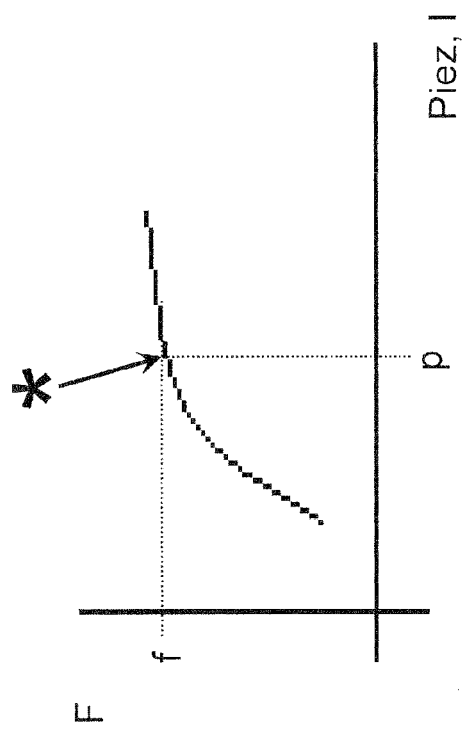
FIG. 17 d illustrates how the force, F, generated by an operator on the inserted ablation catheter relates to piezoelectric forces on the distal end of the catheter's accelerometer (I=current). At the asterisk, the force causes significantly less deformation of the catheter tip (when I=p) and an alert is triggered that notifies the operator that too much force is applied. A dampening mechanism within the catheter handle serves to reduce risk of perforation.
Figure 17:
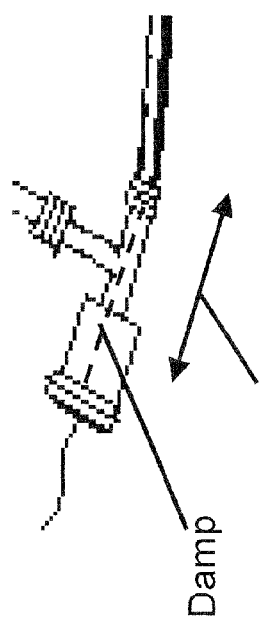
Figure 17F:
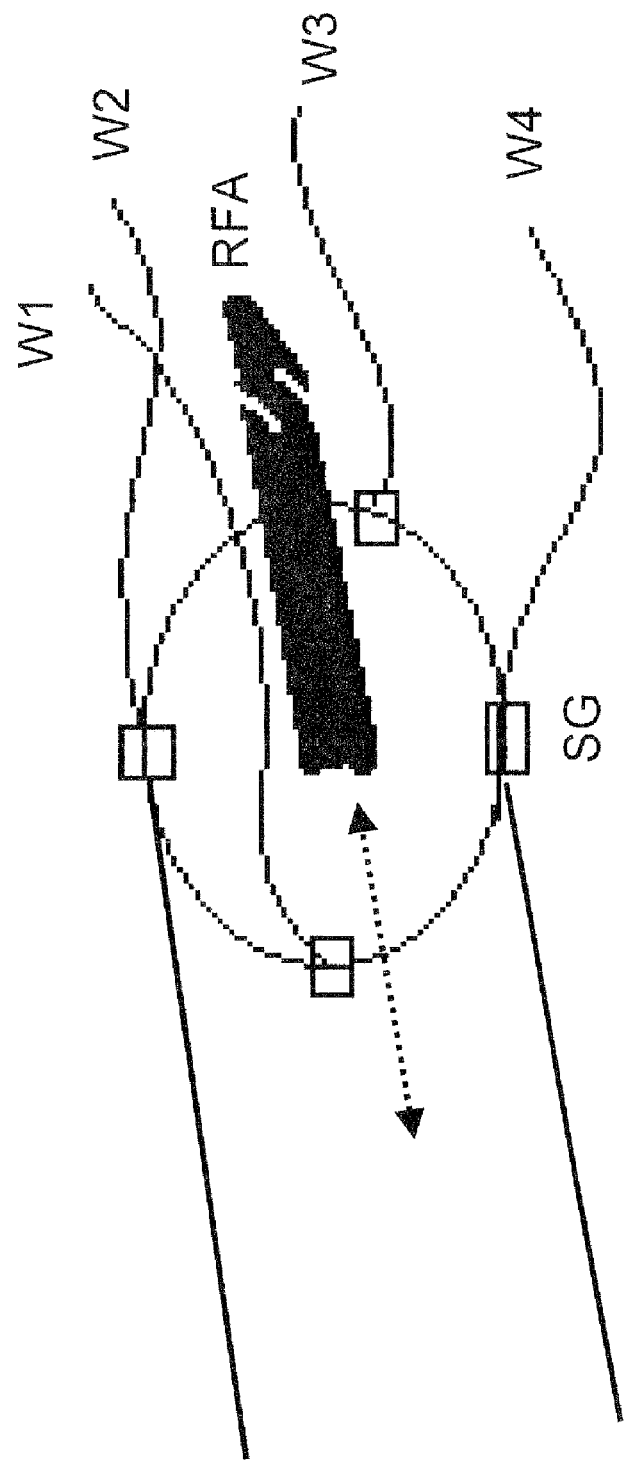
Figure 17G:
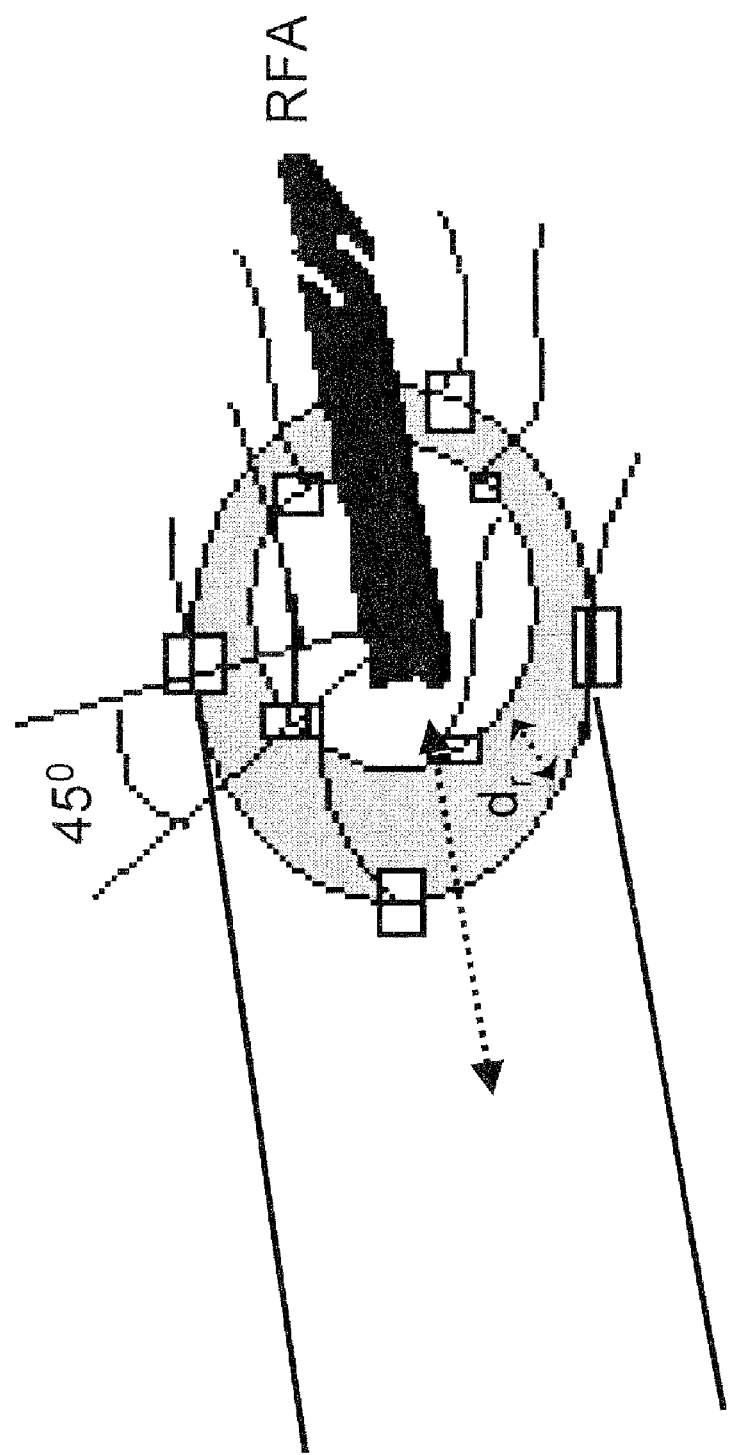

To further elaborate on the capability of the invention, we will describe its application to transeptal puncture techniques (FIG. 17). Those experienced in ablation techniques would be further assisted if they had an appreciation of contact with the inter-atrial septum (IAS) during transeptal puncture. During AF ablation, a catheter or catheters are manipulated from the RA across the IAS into the LA, (preferably across a patent foramen ovale present in approximately 20% of patients). This puncture technique requires careful manipulation of the catheter across the IAS as illustrated in FIGS. 17a and b. Such a catheter design is well known in the art and is comprised of a long vascular sheath similar to that manufactured by companies such as Biosense-Webster (Preface multipurpose) in conjunction with a Brockenbrough needle. In this mode of the invention an accelerometer is juxtaposed along the distal tip of a long vascular sheath and/or Brockenbrough needle.

In a preferred embodiment the needle itself is constructed of material near the tip that has piezoelectric properties. The compliance and deformation properties of the catheter tip, acc, will enable current generation from deformation and reduce risk of tissue damage as depicted in FIG. 17c. Referring to the bottom tracing of FIG. 17b, at time frame B to C, intracardiac pressure tracings are lost as the catheter crosses the IAS (Gonzales M D et al. Transeptal Left Heart Catheterization for Cardiac Ablation Procedures. J Interventional Cardiac Electrophysiology 5, 89-95, 2001). The amount of force generated on the IAS by the operator is unknown and tactile appreciation of this force is limited secondary to the attenuation/damping characteristics of the catheter and surrounding vasculature/tissues. Nonetheless, when the catheter crosses the IAS a characteristic abrupt change in the accelerometer derived signal will occur virtually simultaneously with the corresponding tactile stimulus from the catheter handle.

Figure 18:
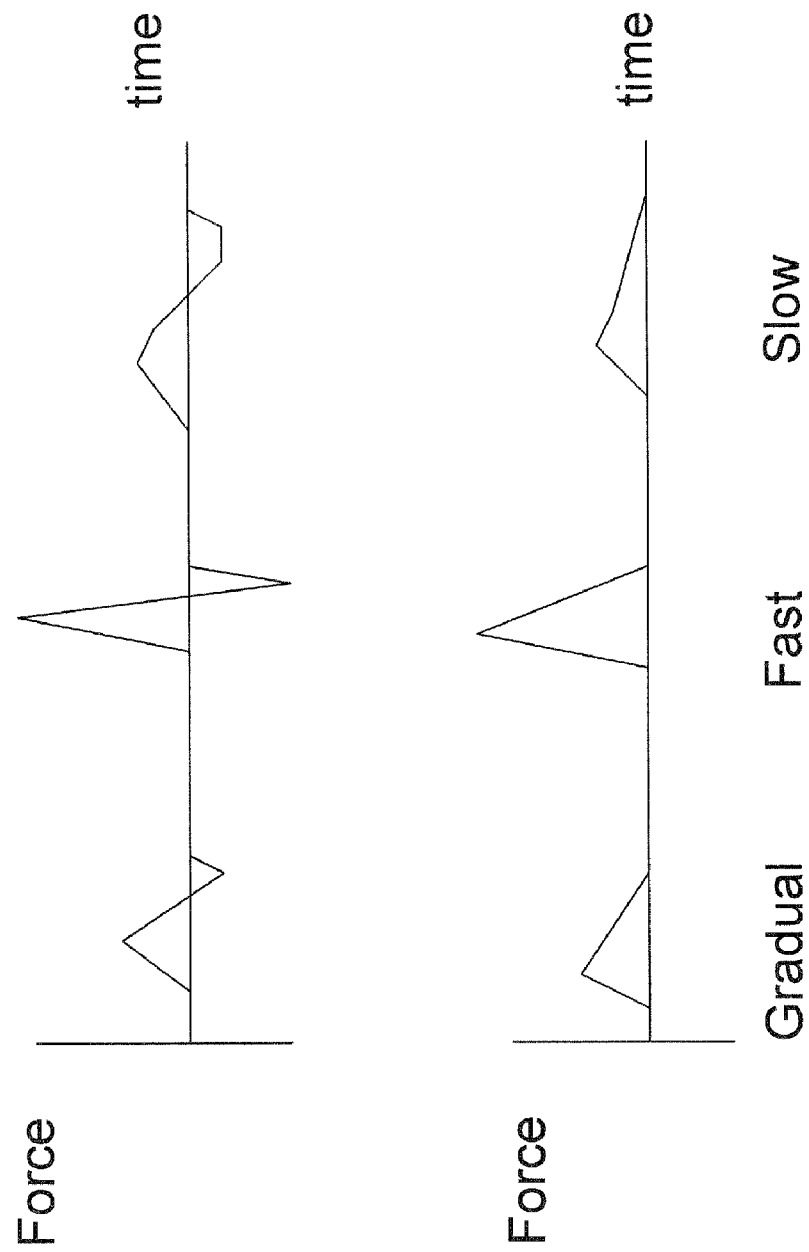
FIG. 18 depicts how different degrees of deformation of the piezoelectric transducer in FIG. 15 and ablation catheter system 16 and needle in 17c translates into proportionate degrees of motion (rectified) of the catheter handle's tactile feedback system. The effects of a gradual, rapid and slow puncture of the IAS are demonstrated. For purposes of explanation and simplification, the top tracing illustrates how the motion of the accelerometer (in one dimension) above and below the axis of the catheter handle is rectified to move the tactile feedback system above a baseline (bottom tracing). More complex systems can be utilized with omnidirectional accelerometers and tactile feedback systems that provide a vibratory movement that resembles the motion of the catheter tip.

In FIG. 18, three examples of transeptal puncture are illustrated. At s, the puncture is slow, at m it is intermediate, and at f it is fast. A gradual puncture of the IAS is preferable as too abrupt of a puncture will increase risk (e.g. greater catheter force) and potentially result in uncontrolled motion that could lead to perforation of other cardiac tissue such as into the aorta, across the atrial free wall and into pericardial space resulting in tamponade and cardiovascular collapse (Gonzales M D et al. Transeptal Left Heart Catheterization for Cardiac Ablation Procedures. J Interventional Cardiac Electrophysiology 5, 89-95, 2001). Thus, determination of catheter/needle location and applied force on the IAS with tactile sensation will vastly improve procedural success and ease such a technique.

The operator will be able to detect when the catheter tip is intra-cavitary, juxtaposed to the IAS, LAA, LA free wall, or near the mitral valve apparatus. A finely tuned accelerometer that has a low threshold for deformation and resultant current formation will be able to appreciate subtle changes in tissue character, especially if the ITES is employed. In a preferred mode of the invention, characteristic changes in the accelerometer/vibrissae derived signal will distinguish the foramen ovale from the surrounding IAS, especially when a patent foramen ovale is present, as inter-atrial blood flow will cause some deformation of a catheter based accelerometer. The system is "taught" how to make such a differentiation by data collection of internally derived signals while numerous patients undergo transeptal punctures under echocardiographic guidance (TEE or intracardiac echocardiography), and in a preferred mode of the invention, via the translation function.

The degree of catheter deflection resulting from increased contact and greater tissue force will be translated in a directly proportionate way to greater displacement appreciated by the operator via the tactile feedback system within the catheter handle. The design of tactile feedback motors are well known in the art of video games and is described in the referenced patents listed herein, though alternate constructs can be implemented as well.

Returning our attention to FIG. 12, analysis of data acquired at I that is extrinsically derived via Doppler ultrasound and data acquired at J can help teach the system's translation function, T, and familiarize the operator about the different tactile sensations possible under varying circumstances. Universal mathematical units of expression (e.g. tissue motion index) that appropriately describe wall motion characteristics are derived by comparing the amplitude of current generated by deformation of lead based accelerometers with units of cm/sec used with tissue Doppler techniques (translation function) as described above. Comparisons of data acquired at I and J from multiple patients will improve the accuracy of such a translation function once many patients have access to this technology.

The examples cited here are applicable when the patient is in AF. During normal sinus rhythm, a characteristic, single organized contraction will be present within the LAA that differs from the tissue about the pulmonary veins. This characteristic impulse is transmitted to the catheter handle in a similar fashion as described above. If this is detected, the operator will have confirmation that the tip of the catheter needs to be relocated and ablation therapy will be switched off.

Any data acquired from the sensors described herein is entered into the CPC along with other data for analysis purposes and treatment recommendations (e.g. future need for anticoagulation). For example, changes in properties of atrial mechanics after ablation therapy will be predictive of risk for recurrence and risk of future thromboembolism and stroke. Higher frequency, lower amplitude tissue motion will correlate with a more delayed recovery of atrial mechanical function and increased risk of thrombus formation. Recommendations about the duration of anticoagulation therapy and need for anti-arrhythmic therapy to suppress recurrent atrial fibrillation are made after integrating such internally derived data with extrinsically derived data (e.g. LA size, hypertension history, patient age etc.) in the algorithms described herein.

Intrinsic/Extrinsic Apparatus

As described in the parent application, a separate intrinsic/extrinsic comparison apparatus (I/E) can function to translate (i.e. derive translation function) and compare analogous indices derived from an implanted device or catheter system and any external diagnostic equipment thereby performing checks and balances for closed loop control systems, CLS (FIG. 19). In FIG. 19 we see how an intrinsic/extrinsic comparison apparatus functions. 700 is any extrinsic apparatus such as an echocardiography machine. 750 is an intrinsic apparatus such as an implanted CRM device or catheter based system inserted into the patient for diagnostic/therapeutic purposes. 800 is the intrinsic/extrinsic apparatus. 850 represents a closed loop system that can be within an implanted device or other diagnostic/therapeutic equipment (e.g. ablation catheter apparatus). 900 and 950 is bi-directional wireless telemetry. Thus, rather than performing the translation function in 400 or at T in 300, I/E can be incorporated into a separate apparatus, be part of an extrinsic imaging device, or be incorporated within an implanted device or catheter system (dashed box in FIG. 19). I/E can be also used to derive common, universal mathematical indices (e.g. motion index) that are representative of degree of normalcy and relates analogous intrinsic and extrinsic physiologic descriptors to prognosis.

The technique and algorithms described are ideal for being incorporated into a robotic system that performs invasive cardiac procedures (e.g. AF ablation, LAA occlusion, percutaneous mitral valve repair).

Data Communication

Parametric imaging techniques can be used to illustrate intrinsically derived data such as time of peak impedance/acceleration/displacement or device based indices of atrial function in addition to cardiac performance as described within the parent application. In the parent application we demonstrated how intrinsically derived indices that are analogous to extrinsically derived data are displayed using color encoded pixels superimposed on images of the heart generated, for example, by echocardiography. In this application of the invention, accelerometer derived indices of tissue motion are displayed in a similar fashion to tissue Doppler derived indices portrayed on state of the art echocardiography machines and reviewed during catheter based procedures and device implantations. Thus, instead of accelerometer type signal display (FIG. 10), the system will generate an image similar to that seen with tissue Doppler or pulse wave Doppler (FIG. 10) which will be more familiar to the operator.

Many other modifications may be made to the invention without departing from its scope as defined in the appended claims.

I claim:

1. A cardiac system comprising:
a catheter having a distal end and a proximal end, said distal end including a sensor configured to contact a portion of a cardiac tissue when said catheter is inserted into said patient, said sensor being configured to sense real time motion of said portion, said real time motion having a real time motion parameter and to generate a corresponding sensor signal having a sensor signal characteristic with a magnitude dependent on said real time motion parameter, said proximal end having a component providing at least one of a vibratory and motion sensation to the hand of an operator holding the handle; and
a processor receiving said sensor signal and transforming said sensor signal into respective haptic representation of the motion of the tissue by driving said component, said haptic representation having an amplitude dependent on the magnitude of said real time parameter.

2. The cardiac system of claim 1 further comprising an external sensor monitoring the cardiac tissue externally and a display generating a corresponding real time image of the position of said distal end.

3. The system of claim 2 wherein said external sensor monitors the cardiac tissue using at least one of ultrasonic, electromagnetic, magnetic, radiographic waves, electrical, impedance data.

4. The system of claim 1 wherein said processor and said component cooperate to generate said haptic representation of at least one cardiac parameter selected from the group consisting of cardiac wall displacement magnitude, cardiac wall velocity, cardiac wall acceleration, blood flow, cardiac acoustic signals, cardiac rotation/torsion, cardiac tissue vibration, frequency of motion, cardiac arrhythmia, cardiac structure and cardiac geometry.

5. The system of claim 1 wherein said internal sensor generates sensor signals indicative of at least one of tissue motion at various frequencies and a motion vector having a magnitude and an angle.

6. The cardiac system of claim 1 wherein said processor is configured to drive said component to provide one of said translation, rotation and vibration wherein said translation, rotation or vibration is proportional to the translation, rotation and vibration of the respective tissue.

7. The cardiac system of claim 1 wherein said haptic representation is indicative of the frequency of the motion of said cardiac tissue.

8. A cardiac system comprising:
a catheter having a distal end and a proximal end, said distal end including a sensor configured to contact a portion of a cardiac tissue when said catheter is inserted into said patient, said sensor is configured to generate sensor signals indicative of a sensed parameter of the real time motion of said portion, said sensed parameter having a real time sensed amplitude, said proximal end having a component providing at least one of a vibratory and motion sensation to the hand of an operator holding the handle, said sensation having a sensation parameter; and
a processor receiving said sensor signal and transforming said sensor signal into a respective haptic representation of at least one cardiac parameter, said cardiac parameter being selected from the group consisting of cardiac wall displacement magnitude, cardiac wall velocity, cardiac wall acceleration, blood flow, cardiac acoustic signals, cardiac rotation/torsion, cardiac tissue vibration, frequency of motion, cardiac arrhythmia, cardiac structure and cardiac geometry, said processor driving said component with said sensation parameter as said sensation parameter.

* * * * *